United States Patent
Sunaoshi et al.

(10) Patent No.: US 8,277,473 B2
(45) Date of Patent: Oct. 2, 2012

(54) MANIPULATOR SYSTEM AND CONTROL APPARATUS

(75) Inventors: Takamitsu Sunaoshi, Yokohama (JP); Makoto Jinno, Ota-ku (JP); Shigeru Omori, Ashigarakami-gun (JP)

(73) Assignees: Terumo Kabushiki Kaisha, Tokyo (JP); Kabushiki Kaisha Toshiba, Tokyo (JP)

( * ) Notice: Subject to any disclaimer, the term of this patent is extended or adjusted under 35 U.S.C. 154(b) by 1217 days.

(21) Appl. No.: 12/061,999

(22) Filed: Apr. 3, 2008

(65) Prior Publication Data

US 2008/0249551 A1    Oct. 9, 2008

(30) Foreign Application Priority Data

Apr. 3, 2007    (JP) .................................. 2007-097753

(51) Int. Cl.
*A61B 17/32* (2006.01)
(52) U.S. Cl. ................. 606/170; 700/245; 901/2; 606/1
(58) Field of Classification Search ................. 340/540; 700/245, 90, 257, 250; 901/2, 6, 8, 14; 414/1, 414/4; 606/1, 170
See application file for complete search history.

(56) References Cited

U.S. PATENT DOCUMENTS

| | | | |
|---|---|---|---|
| 6,238,384 B1 * | 5/2001 | Peer | 606/1 |
| 6,331,181 B1 | 12/2001 | Tierney et al. | |
| 6,850,817 B1 * | 2/2005 | Green | 700/245 |
| 6,994,716 B2 * | 2/2006 | Jinno et al. | 606/170 |
| 6,999,852 B2 * | 2/2006 | Green | 700/245 |
| 7,314,473 B2 | 1/2008 | Jinno et al. | |
| 8,021,358 B2 * | 9/2011 | Doyle et al. | 606/1 |
| 8,142,447 B2 * | 3/2012 | Cooper et al. | 606/130 |
| 2004/0030221 A1 | 2/2004 | Ogawa | |
| 2004/0092912 A1 | 5/2004 | Jinno et al. | |
| 2004/0133189 A1 | 7/2004 | Sakurai | |

FOREIGN PATENT DOCUMENTS

| | | |
|---|---|---|
| EP | 1 439 026 A1 | 7/2004 |
| JP | 2004-105451 | 4/2004 |
| JP | 2004-208922 | 7/2004 |
| WO | WO 2004/029782 A2 | 4/2004 |

* cited by examiner

*Primary Examiner* — George A Bugg
*Assistant Examiner* — Edny Labbees
(74) *Attorney, Agent, or Firm* — Oblon, Spivak, McClelland, Maier & Neustadt, L.L.P.

(57) ABSTRACT

A manipulator has an operation command unit and an exchangeable working unit. The working unit comprises an end effector operable under actions of a control apparatus, and an ID retaining section holding an ID for individualized discrimination of the working unit. The control apparatus includes an ID identification section for identifying the ID and for determining whether the working unit is connected to the operation command unit, an origin point recognition section for recognizing whether the end effector is in a prescribed origin point position or in a non-origin point position, and a warning section which generates a detachment warning when it is determined that the end effector has been detached from the operation command unit, in the event it is determined that the end effector is in a non-origin point position.

20 Claims, 20 Drawing Sheets

MANIPULATOR SYSTEM AND CONTROL APPARATUS

BACKGROUND OF THE INVENTION

1. Field of the Invention

The present invention relates to a manipulator system having a manipulator and a controller, as well as to a control apparatus for controlling a manipulator or the like. In particular, the present invention relates to a manipulator system and a control apparatus, wherein a portion or the entirety of the manipulator is structured so as to be detachable with respect to the controller.

2. Description of the Related Art

In laparoscopic surgery, a number of small holes are opened in a patient's abdomen or the like, and an endoscope, a manipulator (or forceps), or the like is inserted, and surgery is carried out while the surgeon observes an image from the endoscope on a monitor. In this type of laparoscopic surgery, owing to the fact that opening of the abdominal cavity is unnecessary, the burden on the patient is small, and number of days required for the post-operative recovery and number of days spent in the hospital can be significantly reduced. Therefore, laparoscopic surgical operations are expected to find an increased range of applications.

A manipulator system, for example, as disclosed in Japanese Laid-Open Patent Publication No. 2004-105451, comprises a manipulator main body, and a control apparatus for controlling the main body. The manipulator main body comprises an operation command unit and a working unit, which is detachable and exchangeable with respect to the operation command unit.

The working unit includes an elongate connecting shaft, and an end operator (referred to as an "end effector") disposed at the end of the connecting shaft. One or more motors are disposed in the operation command unit for driving the working unit at the distal end by means of wires. The wires are trained around pulleys at a proximal end side. The control apparatus drives the motors and also drives the wires in a circulatory manner via the pulleys.

Because of the necessity to easily clean and disinfect the working unit periodically, the working unit does not contain any electronic components such as sensors or the like, and the positions and origin points of the end effector and the base end pulleys cannot be detected directly. Rather, a structure is provided in which the posture of the end effector is calculated based on a rotation amount of the motors.

Incidentally, in laparoscopic surgery, various different types of working units are used depending on the surgery involved. A gripper, a cutter, an electrical knife, an ultrasonic knife, a surgical drill, or the like may be given as examples thereof. Such working units are disposed detachably with respect to the operation command unit, and when installed, the pulleys on the proximal end side of the working unit engage with rotary axes of the motors disposed in the operation command unit.

In this manner, in the case of a system, which is predicated on enabling the connection of multiple different types of working units with respect to a single operation command unit, it is necessary to set the motor phases such that all of the working units acquire a sole common posture enabling attachment and detachment thereof (see, e.g., Japanese Laid Open Patent Publication No. 2004-105451). Such a posture is referred to as an origin posture (or an initial posture).

Further, when it is desired to exchange the end effector with another type, it is advisable also to exchange the manipulator main body. In this case, a connector, which connects the control apparatus and the operating unit of the manipulator main body, is disconnected, and another connector of a different manipulator main body is reconnected.

With general manipulators available in the industry, although the manipulator and control apparatus are not detached (cut off) while the system is in use (during system operation), it is preferable for detachment (cutting off) between the manipulator and the control apparatus to be easily carried out, since as indicated above, multiple different types of working units are utilized with the manipulator.

In this manner, in the event that the manipulator is to be exchanged with another unit, when the connector is reconnected, generally it is required that the power supply to the control apparatus be switched OFF, and then the connector is detached. This is because, in the operation command unit, an encoder for detecting the angle of rotation of the motors is provided, wherein the circuit for driving the motors is constructed in a closed loop together with the control apparatus, and therefore an open loop condition can happen (referred to below simply as "open loop"), in which motor rotations may occur not as intended, as a result of cutting off the output signal from the encoder midstream.

More specifically, in the connector that interconnects the control apparatus and the manipulator, pins for two motor wires (M+, M−) and four encoder wires (A-phase, B-phase, circuit power source Vcc, Gnd) are provided, and to prevent the occurrence of an open loop, it is necessary that all of these pins be detachable simultaneously, or that the power wires to the motor be cut off before the encoder wires. However, in actual practice, when a connector having a large number of pins is disconnected, not all of the pins can be disconnected at the same time, and an open loop occurs momentarily. Accordingly, when detachment of the aforementioned connector is carried out, it is still required to turn off the power supply of the control apparatus beforehand.

The following may be cited as conventional techniques concerning manipulator systems: Japanese Laid Open Patent Publication No. 2004-105451, Japanese Laid Open Patent Publication No. 2004-208922, and U.S. Pat. No. 6,331,181.

Japanese Laid Open Patent Publication No. 2004-105451 proposes a structure in which it is unnecessary to consider switching of the motor excitation or electrical configurations at the time of detachment.

Japanese Laid Open Patent Publication No. 2004-208922 discloses features related to electrical detachment of plural end tools (working units).

According to U.S. Pat. No. 6,331,181, in relation to attachment and detachment of a medical manipulator, a circuit is included in a front-end manipulator for extracting an ID, wherein controls are carried out by the control apparatus based on obtaining such information.

Incidentally, as described above, the posture of the end effector is calculated taking as a standard the origin position thereof, for example. Accordingly, in the case that the working unit is exchanged during an operation, it is essential for the posture of the newly installed and different working unit to match with the origin position accurately. Stated otherwise, when the working unit is separated from the operation command unit, it is desirable that the working unit be placed in a posture that matches with the origin position thereof.

For this purpose, and so that the working unit cannot be detached except when in its origin position, a method is conceivable, made up of a system that applies a mechanical interlock. However, with such a method, fixing and releasing of the interlock mechanism with each restoration of the origin position must be carried out repeatedly a large number of times, thus making the method complex.

On the other hand, a method may be conceived of by which individual identifying information from each of the working units is obtained, and the motor angles are stored by the control apparatus at a point in time when the units are detached. Then, the next time that a medical device is attached to the control apparatus, but before initiating operation thereof, processing is performed to set the motor phases automatically. However, with this method, the operation command unit is connected to the control apparatus, and by connecting the operation command unit and the working unit, distinct identifying signal lines are connected to the control apparatus. Because IDs are first capable of being acquired at this time, if at the time of connection the motor phases are shifted and a connection cannot be established, the individual information cannot be recognized.

Further, in the event it is desired to exchange the end effector, when the connector is reconnected, generally speaking, the power supply to the control apparatus is turned OFF as discussed previously. However, when the power supply is turned OFF, the connector is detached, and thereafter the power supply to the control apparatus is turned ON again, the computer system inside the control apparatus is reinitiated, so that a certain amount of time is required for rebooting.

Moreover, in Japanese Laid Open Patent Publication No. 2004-105451, no disclosure is provided concerning attachment and detachment of a connector between a manipulator main body and a control apparatus.

In Japanese Laid Open Patent Publication No. 2004-208922, since a closed loop does not exist within the motor control, a device is attached and detached for which changeover of the motor excitation is unnecessary. Although a manipulator is disclosed in the embodiments, the part that is actually attached and detached is simply a tool that is attached to the end of the manipulator. Attachment and detachment of the manipulator itself are not disclosed.

In U.S. Pat. No. 6,331,181, no disclosure is provided with respect to handling when a connector is attached and detached between the manipulator main body and a control apparatus.

SUMMARY OF THE INVENTION

It is one object of the present invention to provide a manipulator system and a control apparatus, which enables detachment of a working unit under a condition in which the operating portion on the working unit is shifted from its prescribed origin position to be identified and drawn to the attention of an operator.

It is one object of the present invention to provide a manipulator system and a control apparatus, in which, in the case that the manipulator is detached from the control apparatus, a stopped state of the actuator can be preserved by means of the manipulator system and the control apparatus.

According to an aspect of the present invention, there is provided a manipulator system equipped with a manipulator and a controller for controlling the manipulator, wherein the manipulator includes an operation command unit for inputting an operation command, and a working unit, which is detachable with respect to the operation command unit, and having an operating member that interacts with and is operated by an actuator of the operation command unit. The working unit includes an ID retaining section, which holds an ID used for individual discrimination of the working units. The controller comprises an ID identification section for identifying the ID of the ID retaining section, a detachment determining section for determining whether or not the working unit has been detached from the operation command unit, based on the ID identified by the ID identification section, an origin point recognition section for recognizing whether the operating member is in a prescribed origin point position or in a non-origin point position, and a warning section, which generates a detachment warning when it is determined, by a judgment of the detachment determining section, that the working unit has been detached from the operation command unit, in the event it is determined that the operating member is in a non-origin point position based on a signal obtained from the origin point recognition section.

According to another aspect of the present invention, there is provided a manipulator system comprising a manipulator equipped with a sensor that detects a position of an operating member, and a controller being connected by a connector to the manipulator. The connector has an electrical power pin, which supplies electrical power to an actuator that operates the operating member, and a signal pin connected to the sensor. The length of each of the pins is set such that, when the connector is detached, the signal pin becomes disconnected after the electrical power pin has been disconnected.

According to still another aspect of the present invention, there is provided a control apparatus for a control object equipped with a sensor that detects a position of an operating member, the control apparatus being connected by a connector to the control object. The connector has an electrical power pin, which supplies electrical power to an actuator that operates the operating member, and a signal pin connected to the sensor. The length of each of the pins is set such that, when the connector is detached, the signal pin becomes disconnected after the electrical power pin has been disconnected.

The above and other objects features and advantages of the present invention will become more apparent from the following description when taken in conjunction with the accompanying drawings, in which preferred embodiments of the present invention are shown by way of illustrative example.

DESCRIPTION OF THE PREFERRED EMBODIMENTS

Descriptions of a manipulator system 500a according to a first embodiment and a manipulator system 500b according to a second embodiment, as working mechanisms according to the present invention, together with control apparatus therefor, shall be presented below with reference to the accompanying FIGS. 1 to 20.

The manipulator system 500a and a control apparatus 514a therefor (see FIG. 1) according to the first embodiment, and the manipulator system 500b and a control apparatus 514b therefor (see FIG. 16) according to the second embodiment, are intended for medical use, and in particular are utilized for performing laparoscopic surgeries and the like.

Figure 1:
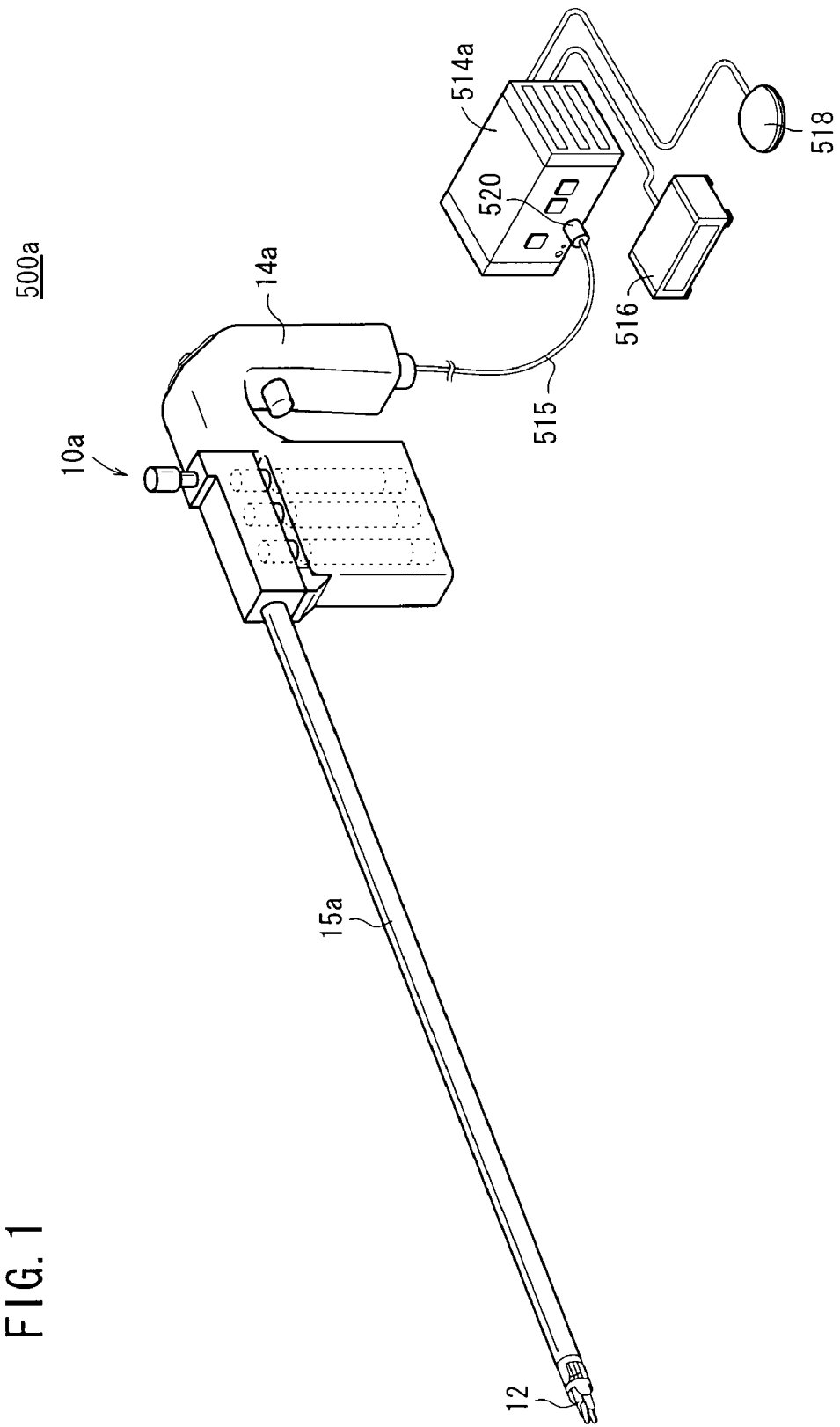
FIG. 1 is an outline structural view of a manipulator system according to a first embodiment of the present invention.

As shown in FIG. 1, the manipulator system 500a includes a manipulator (control object) 10, a control apparatus 514a, and an operating state display device 516, and a command input means 518.

The operating state display device 516, which is connected to the control apparatus 514a, displays the operating state of the manipulator 10, thereby enabling easy recognition of the manipulated state thereof by the surgeon or a surgical assistant. So that the presented result may be easily seen, the operating state display device 516 may be installed alongside an endoscopic monitor.

The command input means 518 serves to carry out instructions (e.g., a temporary stop) of the manipulator 10, and for example, utilizes a footswitch or a voice input means. The command input means 518 may also be disposed as an operating switch on the manipulator main body. Operations of the footswitch, the voice input means, or the operating switch do not interfere with other operations of the manipulator.

The operating state display device 516 and the command input means 518 of the manipulator 10 are connected respectively by cables to the control apparatus 514a. Connectors 520 are provided to make the connections attachable/detachable between the manipulator 10 and the control apparatus 514a. The manipulator 10 causes the end effector 12 to carry out predetermined procedures for gripping a portion of a living body, or for grasping a curved needle, or the like.

Figure 2:
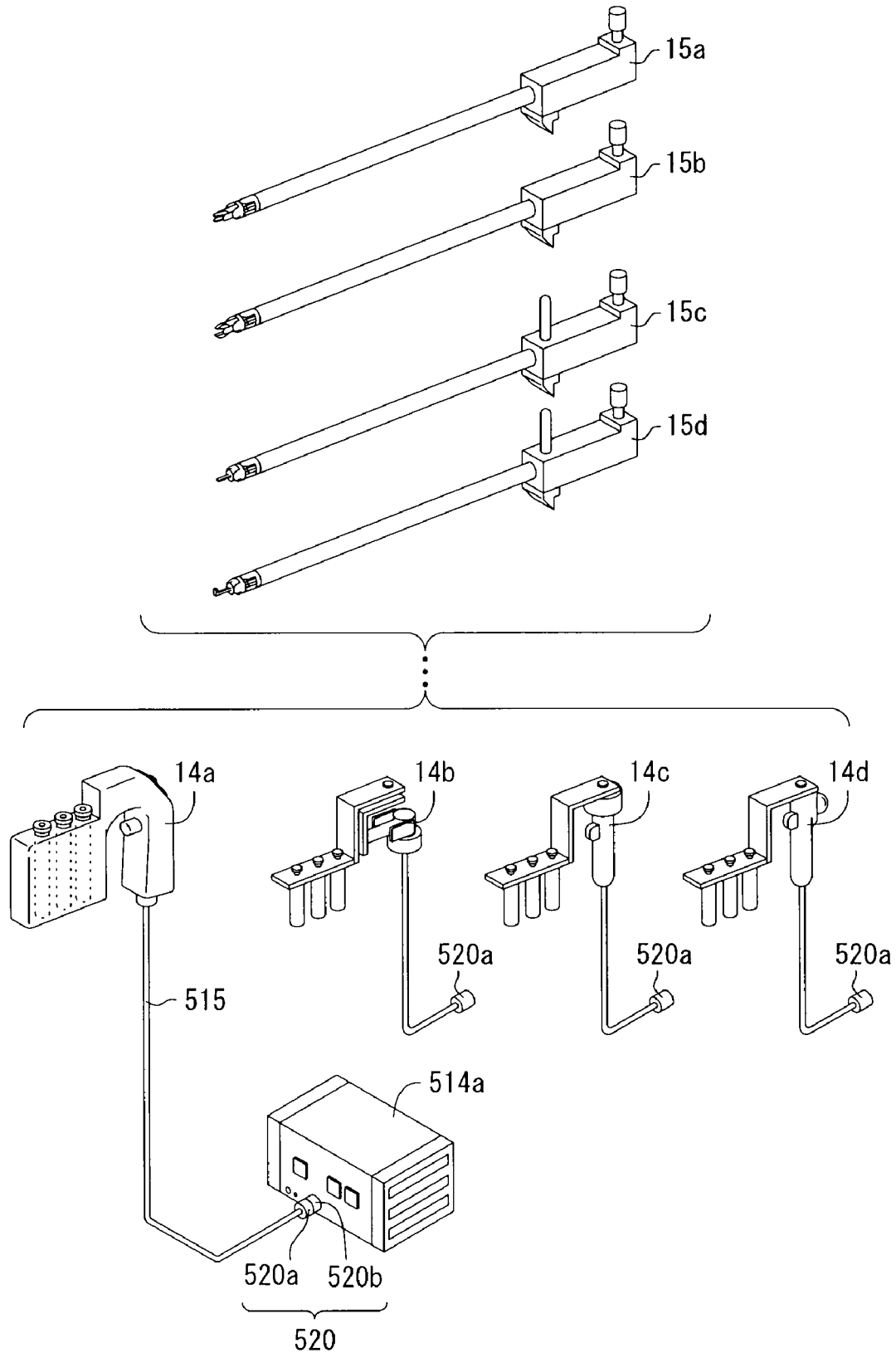
FIG. 2 is an explanatory diagram pertaining to assembly of a structure of the manipulator system according to the first embodiment.

As shown in FIG. 2, the manipulator system 500a may adopt various configurations selectively. Specifically, in the control apparatus 514a, in place of the operation command unit 14a, other different operation command units 14b to 14d may be installed. Further, in place of the working unit 15a, other different working units 15b to 15d can be installed with respect to each of the operation command units 14a to 14d. That is, configurations can be obtained in which the operation command units 14a to 14d (hereinafter referred to collectively as an operation command unit 14) and the working units 15a to 15d (hereinafter referred to collectively as a working unit 15) are combined selectively. Among these, with the working unit 15b, the end effector 12 functions as scissors, with the working unit 15c, the end effector 12 functions as a blade type electrical knife, and with the working unit 15d, the end effector 12 functions as a hook type electrical knife. In each of the working units 15a to 15d, the pulleys 50a, 50b and 50c inside the connector 46 (see FIG. 3) have a common structure and configuration. In the case of the working units 15c and 15d, electrodes are disposed on the upper surface of the connector 46.

Next, the manipulator 10 comprising the operation command unit 14a and the working unit 15a will be described below.

Figure 3:
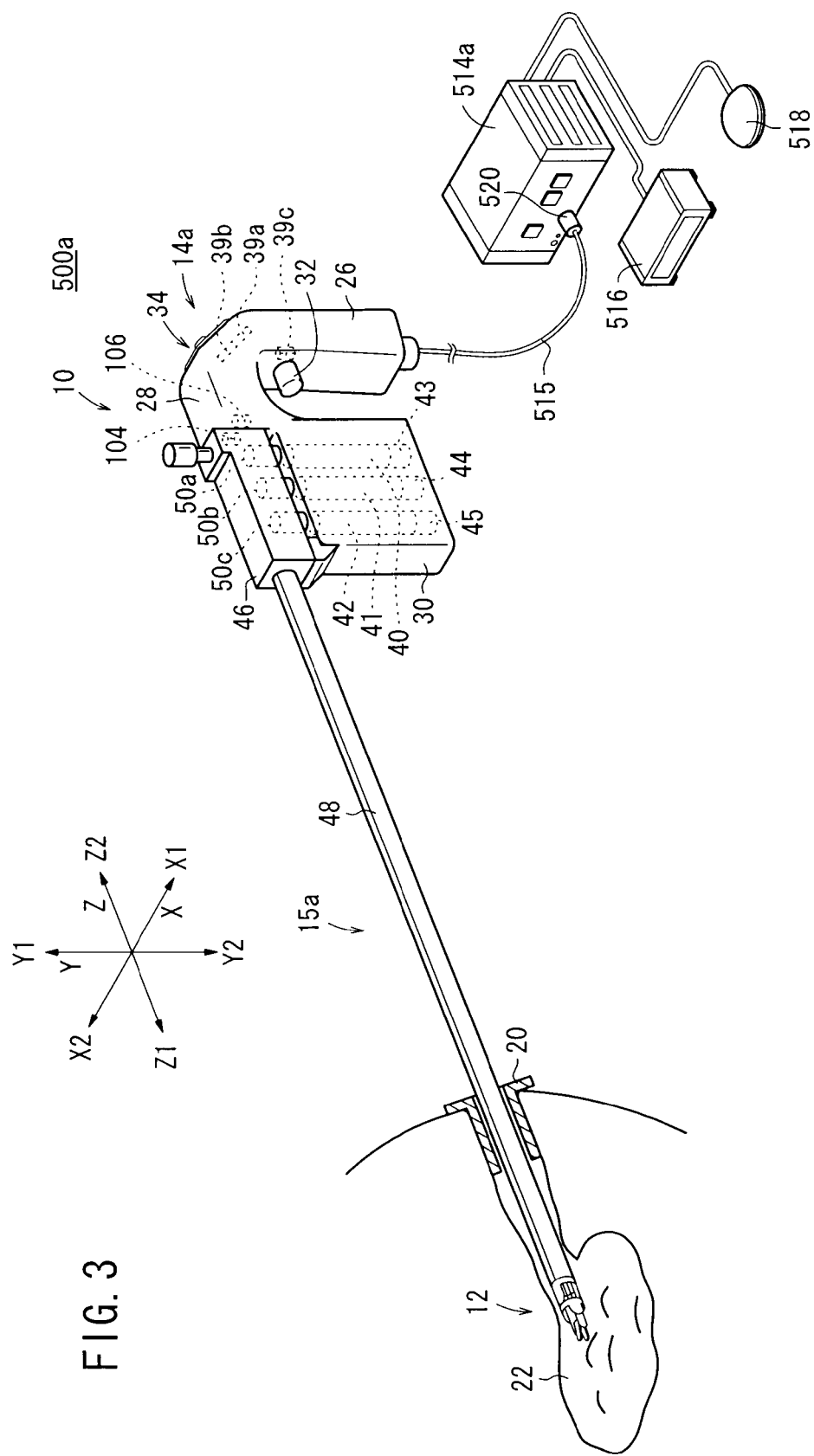
FIG. 3 is a perspective view of a manipulator.

As shown in FIG. 3, the manipulator 10 includes an operation command unit 14a on a proximal end thereof, which is held and operated by the hand, and a working unit 15a, which is detachable with respect to the operation command unit 14a. The working unit 15a comprises an end effector 12 on the distal end thereof for performing operations, and an elongate connecting shaft 48 interconnecting the end effector 12 and the operation command unit 14.

The end effector 12 and the connecting shaft 48 of the manipulator 10 are of a narrow diameter and can be inserted into a body cavity 22 through a trocar 20 in the form of a hollow cylinder mounted in an abdominal region or the like of the patient. Through operating the operation command unit 14, various techniques can be performed to remove, grip, suture, or tie-knot an affected part of the patient's body within the body cavity 22.

It is assumed in the following descriptions that, as shown in FIG. 3, the transverse direction is referred to as an X direction, the vertical direction thereof as a Y direction, and the longitudinal directions of the connecting shaft 48 as a Z direction. Further, among the X directions, the rightward direction is referred to as an X1 direction, and the leftward direction as an X2 direction. Among the Y directions, the upward direction is referred to as a Y1 direction, and the downward direction as a Y2 direction. Among the Z directions, the forward direction is referred to as a Z1 direction, and the rearward direction as a Z2 direction. Moreover, unless otherwise noted, these directions represent directions of the manipulator 10 when it is in an original (origin point) posture. The definitions of the above directions are for illustrative purposes only, and the manipulator 10 can be used in any of various orientations (e.g., the manipulator may be used upside down).

Figure 4:
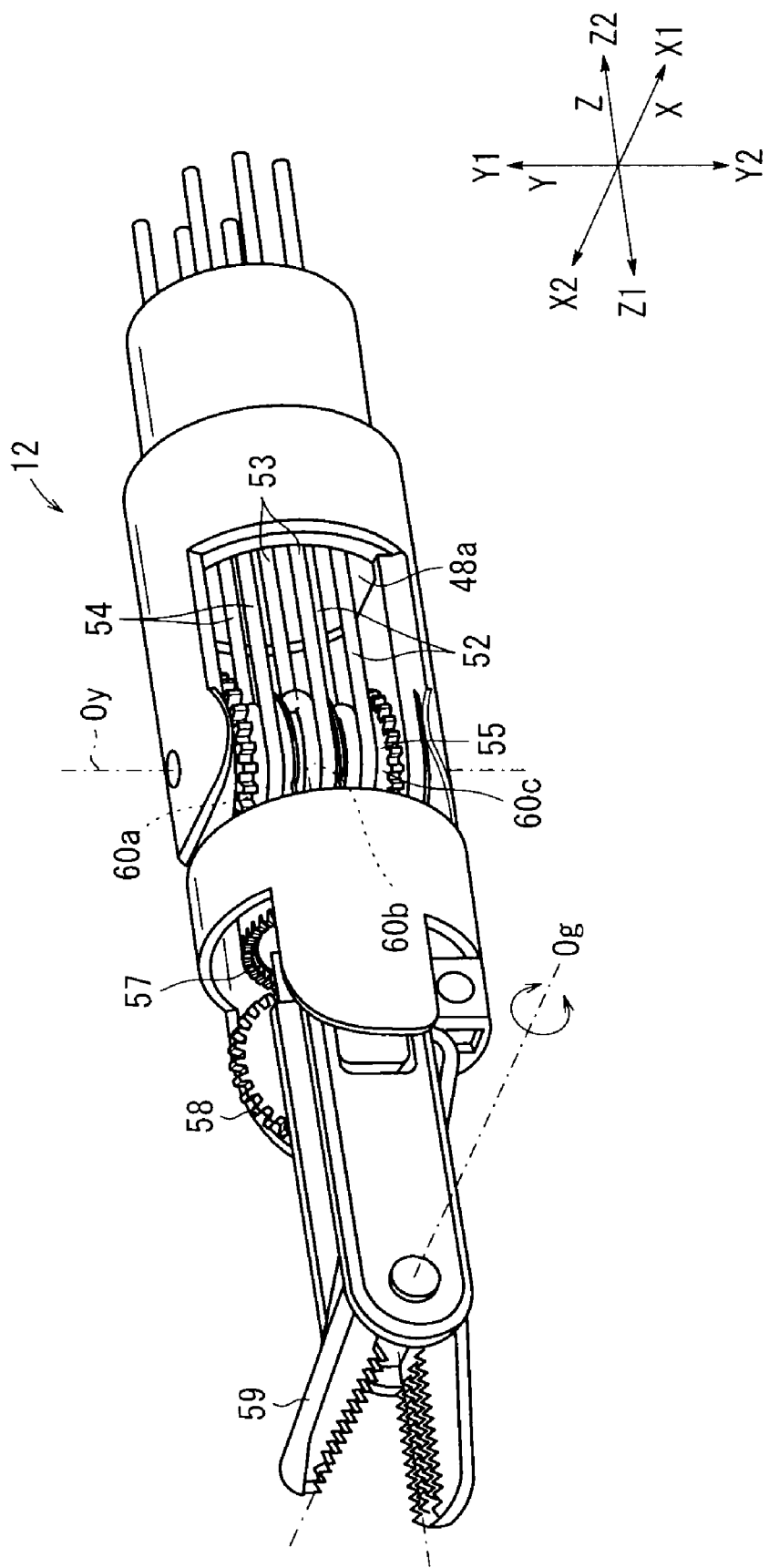
FIG. 4 is a perspective view of an end effector.

The origin point posture is defined beforehand as the state illustrated in FIG. 4, wherein each of the axes is assumed to have a predefined origin point position. In particular, the yaw axis is taken to be in a center position in the left/right direction, while the roll axis is taken to be at a center position about the direction of rotational movement (when the gripper is in an upright position). Further, in the origin point position, the gripper axis is defined as being in a closed condition. Assuming such origin positions as standard positions, each of the axis angles is calculated from the integrated angles of the motors.

The operation command unit 14 includes a grip handle 26 gripped by hand, a bridge 28 that extends from an upper portion of the grip handle 26, and an actuator block 30 connected to a distal end of the bridge 28. The lower end of the grip handle 26 may also be connected to a lower end of the actuator block 30.

The grip handle 26 extends in the Y2 direction from the end of the bridge 28, with a length that is suitable for being gripped by the hand, and includes a trigger lever (input means) 32 that serves as an input means, and a compound input section (input means) 34. The trigger lever 32 projects downwardly of the bridge 28 slightly in the Z1 direction, and is disposed in a position that enables a pulling action to be performed easily by the index finger.

The compound input section 34 serves as a compound input means, which gives rotation commands in rolling directions (the direction of axial rotation) and yawing directions (left/right lateral directions) with respect to the end effector 12. For example, a roll direction command can be carried out by a first input means for moving in vertical directions, and a yaw direction command can be carried out by a second input means for moving in lateral directions. Input sensors 39a, 39b, 39c (see FIG. 3) are provided on the trigger lever 32 and the compound input section 34 for detecting respective movement amounts, wherein the detected movement signals (e.g., analog signals) are supplied to the control apparatus 514a.

The actuator block 30 houses therein three motors 40, 41, 42 corresponding to respective mechanisms offering three degrees of freedom, which are incorporated in the end effector 12. The motors 40, 41, 42 are arrayed in parallel in the longitudinal direction of the connecting shaft 48. The motors 40, 41, 42 are small in size and narrow in diameter, thereby making the actuator block 30 compact and flat in shape. The actuator block 30 is disposed downwardly of the end of the operation command unit 14, in the Z1 direction. In addition, the motors 40, 41, 42 rotate under the control of a control apparatus 514a based on operations of the operation command unit 14.

Angle sensors 43, 44, 45, which can detect the angles of rotation thereof are disposed in the motors 40, 41, 42. The detected angle signals are supplied to the control apparatus 514a. Rotary encoders, for example, may be utilized as the angle sensors 43, 44, 45.

The control apparatus 514a serves to control the manipulator 10 electrically, and is connected through a connector 520 to a cable 515 extending from the lower end of the grip handle 26.

The working unit 15a includes a connector 46 joined to the actuator block 30 and a hollow connecting shaft 48 extending in the Z1 direction from the connector 46. The connector 46 houses therein a pulley 50a, a pulley 50b, and a pulley 50c, which are rotatable and connected respectively to the drive axes of the motors 40, 41, 42. Couplings are disposed respectively on the pulleys 50a, 50b and 50c.

A wire 52, a wire 53, and a wire 54 are trained respectively around the pulleys 50a, 50b, 50c, and extend through a space 48a (see FIG. 5) in the connecting shaft 48 to the end effector 12. The wires 52, 53 and 54 may be of the same type and same diameter.

The connector 46 can be operated according to a predetermined process to disconnect the working unit 15a from the operation command unit 14 for cleaning, sterilization, maintenance, and the like. Further, the end portion from the connector 46 is replaceable. For example, depending on the technique required for a certain surgical operation, the connector 46 may be replaced with a connector having a different length and/or the end effector 12 may be replaced with an end effector incorporating different mechanisms.

Figure 5:
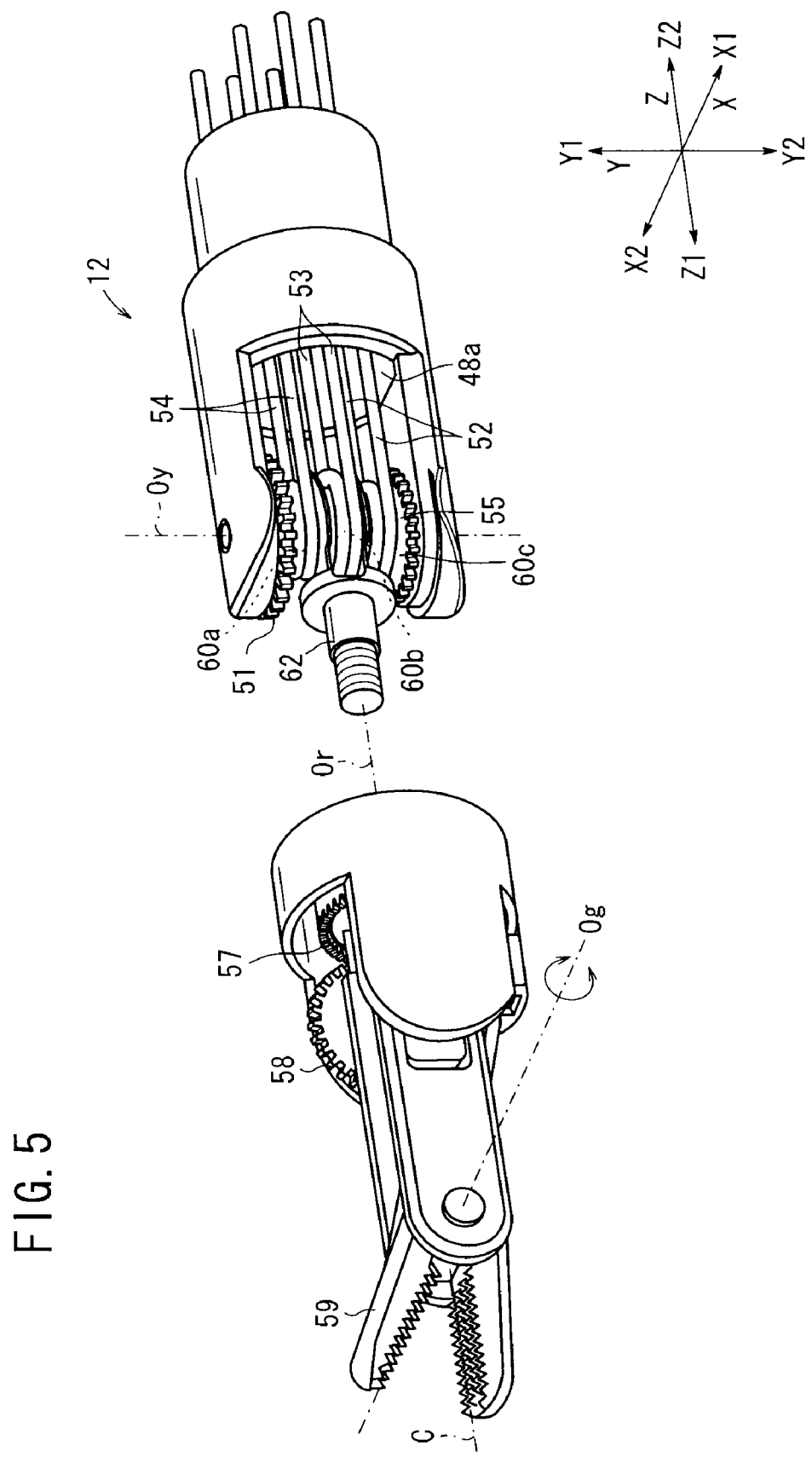
FIG. 5 is an exploded perspective view of the end effector.

As shown in FIG. 5, the end effector 12 includes mechanisms providing three degrees of freedom in total, made up of a mechanism (tilting mechanism, pivot shaft) having a first degree of freedom for rotating a portion of the end effector 12 that is positioned ahead of a first rotational axis Oy extending along the Y direction, in yawing directions, a mechanism (roll-rotating mechanism) having a second degree of freedom for angularly moving the portion of the end effector 12 in rolling directions about a second rotational axis Or, and a mechanism having a third degree of freedom for opening and closing a gripper (opening/closing mechanism) 59 on the distal end of the end effector 12 about a third rotational axis Og.

The first rotational axis Oy made up of the mechanism having the first degree of freedom may be set so as to be capable of rotation in a non-parallel fashion with an axis C that extends from the proximal end to the distal end of the connecting shaft 48. The second rotational axis Or made up of the mechanism having the second degree of freedom comprises a rotating mechanism, which is capable of rotating about an axis of a direction extending from the distal end portion (i.e., the gripper 59) on the end effector 12, and may be set so as to enable rotation of the distal end portion in rolling directions.

The end effector 12 is driven by respective wires 52, 53 and 54. Each of the wires 52, 53 and 54 is wound respectively around corresponding cylindrical bodies 60c, 60b, 60a.

At the end effector 12, respective gears 51 and 55 are rotated by the wires 52 and 54, and by rotation of a non-illustrated face gear, the distal end portion can be rotated in rolling directions. Further, the gear 51 is rotated by the wire 54, thereby to enable opening and closing of the gripper 59 through a face gear 57 and a gear 58. Furthermore, through a main shaft member 62, the distal end portion can be rotated in yawing directions by the wires 52, 53 and 54.

Figure 6:
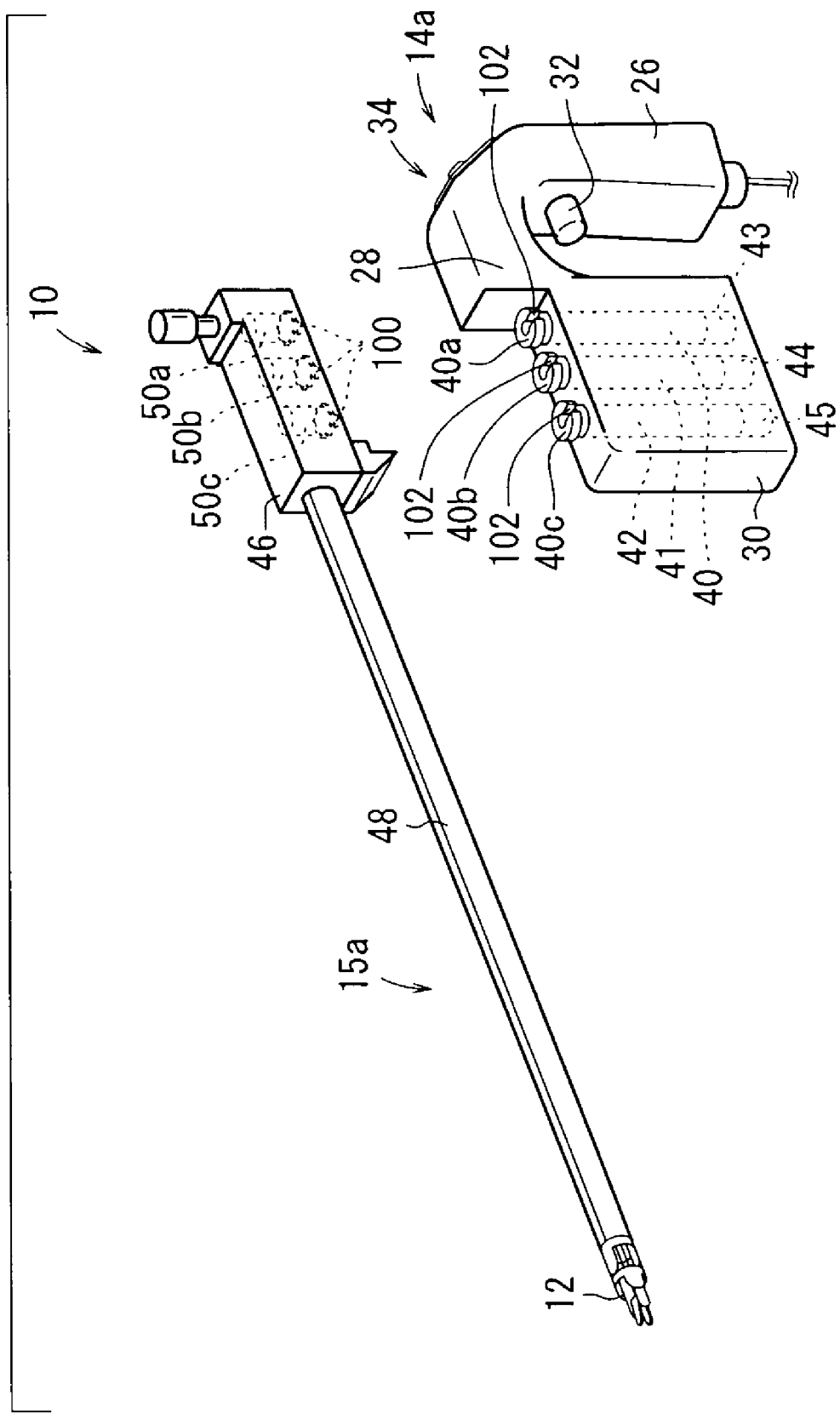
FIG. 6 is a perspective view of a manipulator in which a working unit and an operation command unit are separated.
Figure 7:
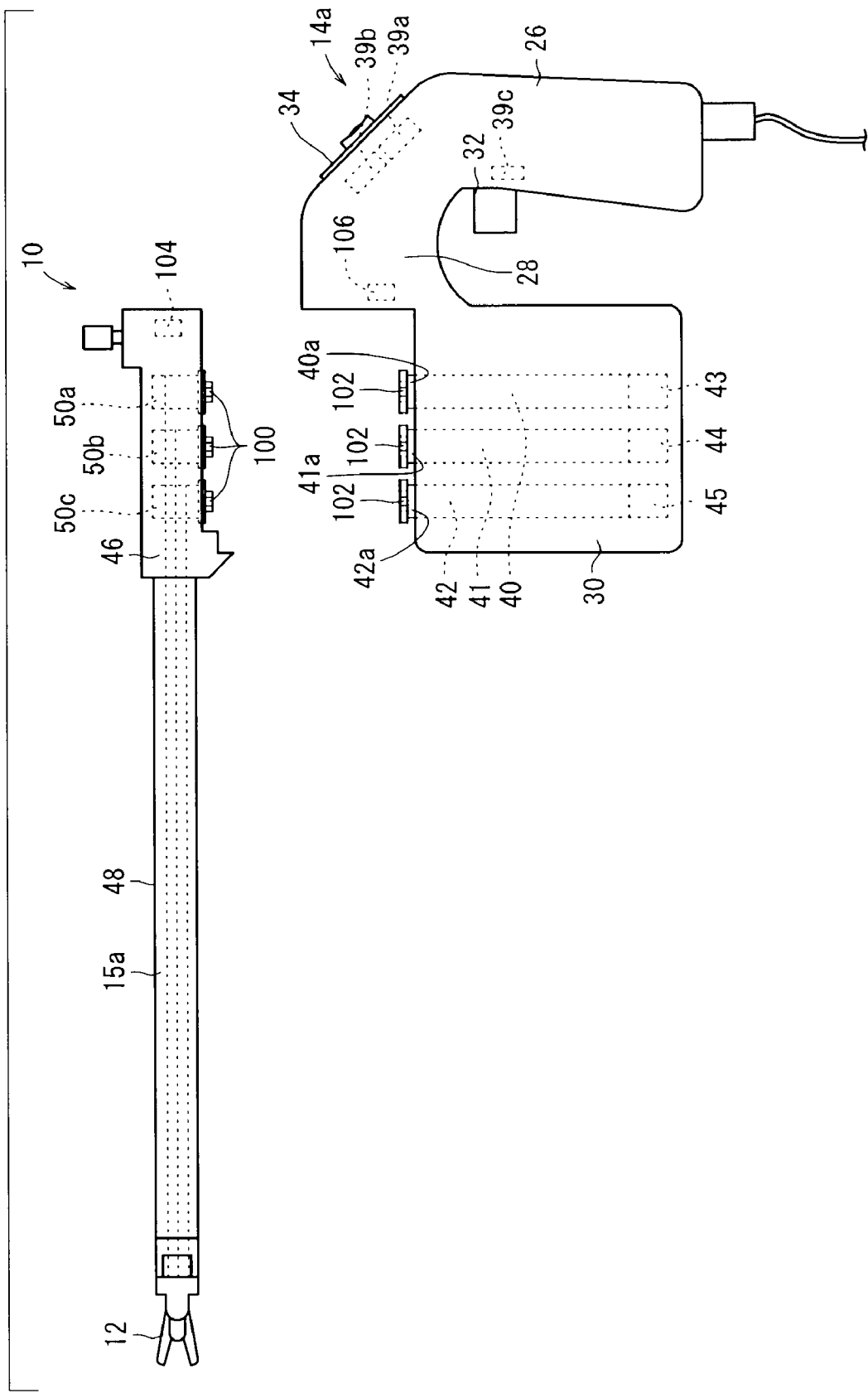
FIG. 7 is a side view of the manipulator in which the working unit and the operation command unit are separated.

As shown in FIGS. 6 and 7, the working unit 15a is detachable from the operation command unit 14a, and the rotational axes 40a, 41a, 42a of the motors 40, 41, 42 are configured so as to be fitted into central holes of the pulleys 50a, 50b and 50c. An engaging projection 100 is provided on each of the central holes of the pulleys 50a, 50b, 50c, whereas engaging recesses 102 are provided respectively on the rotational axes 40a, 41a and 42a. The engaging projections 100 and engaging recesses 102 are capable of mutual engagement with each other, whereby rotations of the motors 40, 41, 42 are reliably transmitted to the pulleys 50a, 50b and 50c. Further, the engaging projections 100 and engaging recesses 102 are constituted such that engagement thereof other than at the origin point posture does not occur.

An ID retaining section 104, which retains an ID that can distinguish between each of the working units 15a to 15d, is provided on the connector 46. The ID retaining section 104 has a 3-bit structure. Each bit of the ID retaining section 104 is distinguished by "1" or "0" based on the presence or absence of magnetism. That is, bits for which magnetism is present are active and recognized as "1", whereas bits for which magnetism is not present are negative and recognized as "0". The meaning of "negative" herein implies a natural state, i.e., a state in which the status thereof does not change between a case where the working unit 15 is attached to the operation command unit 14 and a case where the working unit 15 is detached from the operation command unit 14. The meaning of "active", by contrast, implies a state in which the status thereof changes between the above two cases.

The respective bit portions of the ID retaining section 104 are not limited to magnetic types, and for example, may also be constituted as a wireless type made up of RFID (Radio Frequency Identification), an optical non-contact detection type formed by bar codes or a matrix type of two dimensional codes, or a contact type made up of an array of small projections or the like. Also, the bit number of the ID retaining section 104 is not limited to 3-bits per se.

In the case that a writable memory means, such as an RFID or like, is utilized on the working units 15a to 15d, individualized information, made up of a time stamp or serial number indicating the manufacturing date, the date of first use, the date of last use, and the maintenance period, etc., the usage cycle upper limit, a phase correction value (or an origin-point correction value) or the like, may be recorded on a case by case basis. Such information is read in by the control apparatus 514a and displayed on the operating state display device 516, and further, by carrying out predetermined judgments, various cautions or warnings may be generated.

In the retaining sections 104, the working units 15a to 15d store the respective bit values $011_b$, $101_b$, $110_b$, and $111_b$ as IDs (the suffix "b" indicates binary number). In other words, each of the working units 15a to 15d is given a different ID that enables it to be distinguished from the others, and moreover, in each of the IDs, a "1" bit is provided for two or more of the bits thereof. Further, in the event that the ID is 4 bits or greater, the "1" bits are set so as to make up half or more of the total bit number (e.g., in the case of 4 total bits, the "1" bits make up 2 bits or more).

Incidentally, it is not necessary for the ID retaining section to be electrically energized, and no electrical components exist within the connector 46 and the working units 15. Accordingly, cleaning and sterilization or the like can easily be carried out on the working units 15 when detached from the operation command unit 14. More specifically, electrical components such as motors, switches, sensors and the like are all arranged on the side of the operation command unit 14, and by disposing the connecting shaft 48 and end effector 12, which are made up only of mechanical elements, all on the side of the working unit 15, the device can be cleaned more easily. The manner and types of ways under which the working unit and the operation command unit become dirty or contaminated, as well as the cleaning methods therefor, differ from one another, and thus in order to carry out different maintenance operations thereon, it is preferable to enable them to be detachable from each other.

The operation command unit 14 includes an ID relay (ID detector) 106 which reads the respective bits in the ID retaining section 104 of the working unit 15 connected thereto and supplies them to the control apparatus 514a. The ID relay 106 comprises a magnetic sensor for detecting the magnetism pertaining to each bit of the ID retaining section 104. Further, in the case that each bit portion of the ID retaining section 104 is configured as an array of small projections, the ID relay 106 may be constituted by small switches, which are operated respectively by the small projections.

When a magnetic, optical or electrical wave method is utilized, the ID retaining section 104 can transmit the ID in a non-contact manner with respect to the ID relay 106, whereby the durability of the ID retaining section 104 and the ID relay 106 is heightened, contamination is reduced, and cleaning and washing thereof is made easier.

Figure 8:
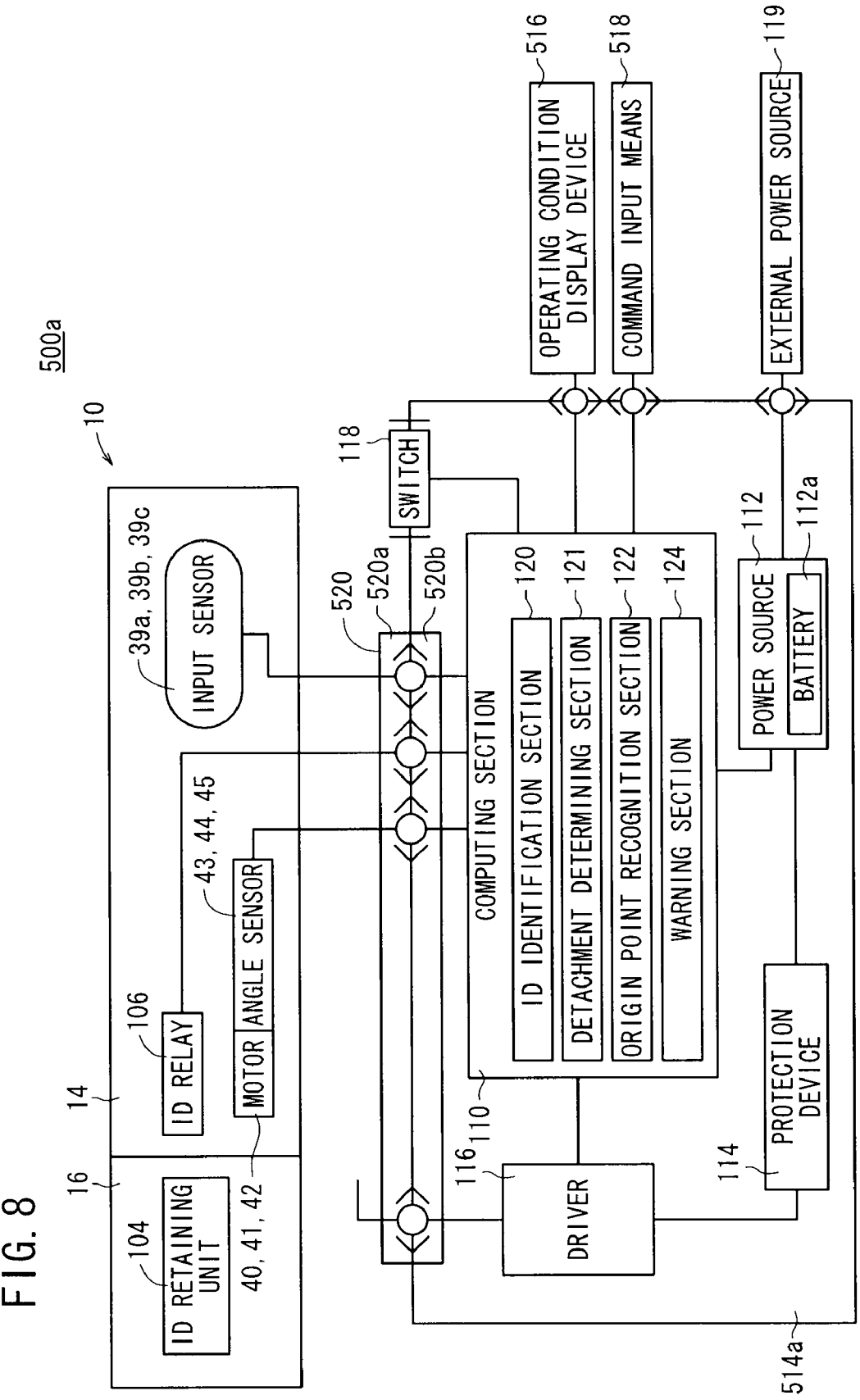
FIG. 8 is a structural block diagram of a control apparatus for the manipulator system according to the first embodiment.

As shown in FIG. 8, the control apparatus 514a includes a computing section 110, a power supply 112, a protection device 114, a driver 116, and a switch 118. The power supply 112 rectifies electrical power obtained from an external power source 119 and supplies electrical power to respective components, together with performing charging of a battery 112a. A function is included therein such that, even in the case that electrical power is not supplied from the external power source 119, switching is performed automatically to supply power from the battery 112a, so that the power supply 112 operates as a so-called uninterrupted power source. The battery 112a may be connected, either in series or in parallel, with respect to a transformer/rectifier therein.

The protection device 114 serves to interrupt supply of power to the manipulator 10 based on various information such as computational period information from the computing section 110, driver information, predetermined stop commands and the like. By interrupting the electrical power of the driver 116 under operation of the protection device 114, actions of the manipulator 10 can be instantaneously halted.

The switch 118 is utilized for switching commands of the operational state of the manipulator 10, power source switching, etc.

The computing section 110 is connected to angle sensors 43, 44, 45, input sensors 39a, 39b, 39c, a command input means 518 and to the switch 118, and based on signals obtained from each of these components, determines operations of the manipulator 10 and supplies predetermined command signals to the driver 116, while also indicating predetermined state amounts to the operating state display device 516. The computing section 110 is constituted from components such as a CPU, a ROM, RAM memory, etc., wherein by reading and executing a program, a predetermined software based process is carried out thereby.

The driver 116 is connected to the motors 40, 41, 42 and drives the motors 40, 41, 42 based on commands obtained from the computing section 110. Incidentally, as for the drive system for the motors 40, 41, 42, first, operation angle command values with respect to the end effector are determined based on the input sensors 39a, 39b, 39c, deviations between such operation angle command values and the angle signals obtained from the angle sensors 43, 44, 45 are determined, and then based on such deviations, a predetermined compensation process is performed and command signals are supplied to the driver 116. Accordingly, the drive system for each of the motors 40, 41, 42 is formed as a closed-loop system.

The computing section 110 includes an ID identification section 120, a detachment determining section 121, an origin point recognition section 122, and a warning section 124. The ID identification section 120 identifies the ID of the ID retaining section 104. The detachment determining section 121 determines whether or not the working unit 15 has been detached from the operation command unit 14 based on the ID recognized by the ID identification section 120.

More specifically, since the ID obtained from the ID identification section 120 is configured by 3 bits, the ID enables $2^3=8$ units to be distinguished, however, among these, the bit data $000_b$ is identified as a state in which none of the working units 15a to 15d is connected whatsoever. That is, in the event that none of the working units 15a to 15d is connected, each of the bits becomes negative, whereupon the detectors corresponding to each bit of the ID relay 106 do not detect any magnetism and "0" values for each are supplied to the control apparatus 514a. Moreover, with the ID identification section 120, when the recognized ID changes, it is judged that a working unit 15 has been detached. Specifically, when any one of the bits switches from "1" to "0" (the "1" value is provided for two or more of the 3 bits of the ID, as described above), it is recognized that one of the working units 15a to 15d has been detached. Owing thereto, detachment of the working units 15a to 15d can be recognized quickly, and a predetermined corresponding process can be promptly carried out.

The computing section 110 determines conditions based on other signals from the ID identification section 120, the origin point recognition section 122, and the operation command unit 14, and stops supplying electrical power to the driver 116 under predetermined conditions, whereupon the motors 40, 41, 42 are rendered non-excited. As a means for causing non-excitation of the motors 40, 41, 42, a relay or the like also may be used, wherein decoupling between the driver and the connector 520 may be effected by such a relay.

Among such conditions, a condition in which a predetermined time elapses while the end effector 12 of the working unit 15 remains in the origin point position may be given as a first condition. At such times, it may be judged that operations of the manipulator 10 are temporarily halted, or that preparations are being made to detach the working unit 15, and accordingly, deenergizing of the motors 40, 41, 42 is favorable. As a result, even when the working unit 15 is separated from the operation command unit 14, the motors are non-energized, and thus unnecessary movement of the pulleys 50a to 50c does not occur.

Further, a condition wherein the working unit 15 actually is separated from the operation command unit 14 may be given as a second condition. At such times, by keeping the motors 40, 41, 42 in a non-excited state, unnecessary movement of the rotational axes 40a, 41a, 42a is prevented, and predetermined standard angles therefor are maintained.

Furthermore, a condition wherein the operation command unit 14 actually is detached from the control apparatus 514a may be given as a third condition. At such times, by stopping the supply of power to the driver 116, power is not consumed in the driver 116, and voltage is not imposed unnecessarily with respect to the electrical power pins 152 (see FIG. 9) of the connector 520.

Moreover, the third condition can be determined based on signals obtained from the input sensors 39a, 39b, 39c of the trigger lever 32 or the compound input section 34. More specifically, these signals are configured to exhibit voltage values within a predetermined range when the operation command unit 14 is connected. When the operation command unit 14 is disconnected, the voltage values become 0V by means of a pull-down circuit, thereby enabling the detachment to be determined.

Stated otherwise, in the trigger lever 32 and compound input section 34, predetermined voltages are imposed on detectors (potentiometers or the like), which serve to detect the amounts by which the trigger lever 32 and the compound input section 34 are manually operated. The predetermined ranges of such voltages are set as operating ranges thereof, and the control apparatus 514a recognizes that the operation command unit 14 has been detached based on the voltages supplied from the detectors being outside of the predetermined ranges. Accordingly, both the trigger lever 32 and the compound input section 34 can be used dually as an operating amount input means, as well as a detachment recognition means for the operation command unit 14. Further descriptions shall be given below concerning processing that takes place upon detachment of the operation command unit 14.

Because a large amount of power consumption is expended to excite the motors, by halting the supply of electrical power to the driver 116 in accordance with the above first through third conditions, the power consumption of the system can be reduced. In the case that backup power in a hospital is utilized upon occurrence of a wide scale power outage, the power consumption of the backup power source can favorably be suppressed. Further, even in the event that the battery 112a inside the control apparatus 514a is operated during a power outage within the hospital, the power consumption of the battery 112a can be suppressed, enabling the surgical procedure to continue, while ample time for a retraction operation of the manipulator can be assured.

Incidentally, three methods may generally be contemplated as methods for stopping the motors. The first method, which is referred to as SERVO OFF, is a method by which excitation of the motors is cut off and the motors are released by means of circuitry. Such a SERVO OFF method is a function of the motor driver, and it is necessary for a circuit power source to be supplied to the driver. In this method as well, the configuration and procedures therefor are simple and reliability is high, and the consumption of energy can be made small with certainty. Further, in the case that a watchdog function is employed for monitoring the operating condition of the computer, it is preferable to halt the motors by means of this method.

For example, the first method is suitable in the case that the speed reduction ratio in a motor is set to be large, and it can be determined that movement by an ordinary external force will not occur.

The second method is one by means of an electromagnetic break caused by short-circuiting, which generally is a function provided in the motor driver. This is a function whereby the same voltage is applied to both terminals of the motor for electrically stopping the motor. When the motor is released, unnecessary movement is prevented when a load is added to a concerned part thereof.

The second method is suitable when the speed reduction ratio is small, or when an external force constantly is added to the motor axis and movement thereof by the external force is prevented.

The third method is one by which electrical power of the motor driver is cut off. Even in cases where it may be difficult to apply the first and second methods, it is still possible to stop the motors, and in such a case, the third method is preferably used to stop the motors. Depending on the circumstances, it is a matter of course that the first through third methods may also be used in combination, as well as separately.

Further, when the first through third conditions arise, the computing section 110 supplies a stop signal to the driver 116.

Herein, the stop signal is defined as a command signal to cause the motors not to rotate whereupon, for example, 0V is supplied. Further, in accordance with the driver 116, a case exists in which a 0V to 5V specification is used. In this case, an intermediate 2.5V signal may be supplied as the stop signal.

When it is recognized that the operation command unit (motor) 14 and the control apparatus 514a are disconnected, and moreover, in the case that the control apparatus 514a is operated by a backup power source, it is preferable for the stop signal to be in the vicinity of 0V in order to reduce the consumption current. This is because the output voltage in a DA (digital/analog) circuit of the interface being 0V causes consumption of the circuit power source to decrease. However, even in the case that 2.5V is supplied as the stop signal to the motor, as described previously, a configuration is acceptable in which the DA circuit outputs 0V and establishes an offset via circuitry.

In accordance with the foregoing, the motors 40, 41 and 42 can be placed in a non-excited condition more reliably. In addition, when the first through third conditions arise, the excitation of the motors 40, 41 and 42 may be even further decreased, the gain in the control loop of the motors 40, 41 and 42 may be lowered in the computing section 110, and the PID constants may also be varied as desired.

The origin point recognition section 122 recognizes whether the end effector 12 is in a regulated (standard) origin point position or is in a non-origin point position. In the event it is determined that the end effector 12 is in a non-origin point position based on a signal obtained from the origin point recognition section 122, the warning section 124 generates a detachment warning when it is judged that the working unit 15 has been detached from the operation command unit 14 based on the ID obtained from the ID identification section 120.

Further, when the detachment warning is generated, the warning section 124 monitors the ID obtained from the ID identification section 120, and thus recognizes when one of the working units 15a to 15d is reconnected. Then, if the obtained ID is the same as the ID recognized before the detachment occurred, the warning section 124 cancels the warning, or alternatively, the warning section 124 generates a misconnection warning if the obtained ID is different from the ID that was recognized prior to detachment.

The detachment and misconnection warnings can be carried out by an acoustic/sound means or by a visual means such as the operating state display device 516. It is preferable for the detachment warning and the misconnection warning to be easily distinguished from each other, for example, by means of buzzer sounds that differ in their siren interval or in frequency.

In the event it is determined, by the ID identification section 120, that the working unit 15 has been detached, or if it is determined, by the origin point recognition section 122, that the end effector 12 is in the origin point position, the computing section 110 stops the supply of electrical power to the driver 116 under an action of the protection device 114.

Figure 9:
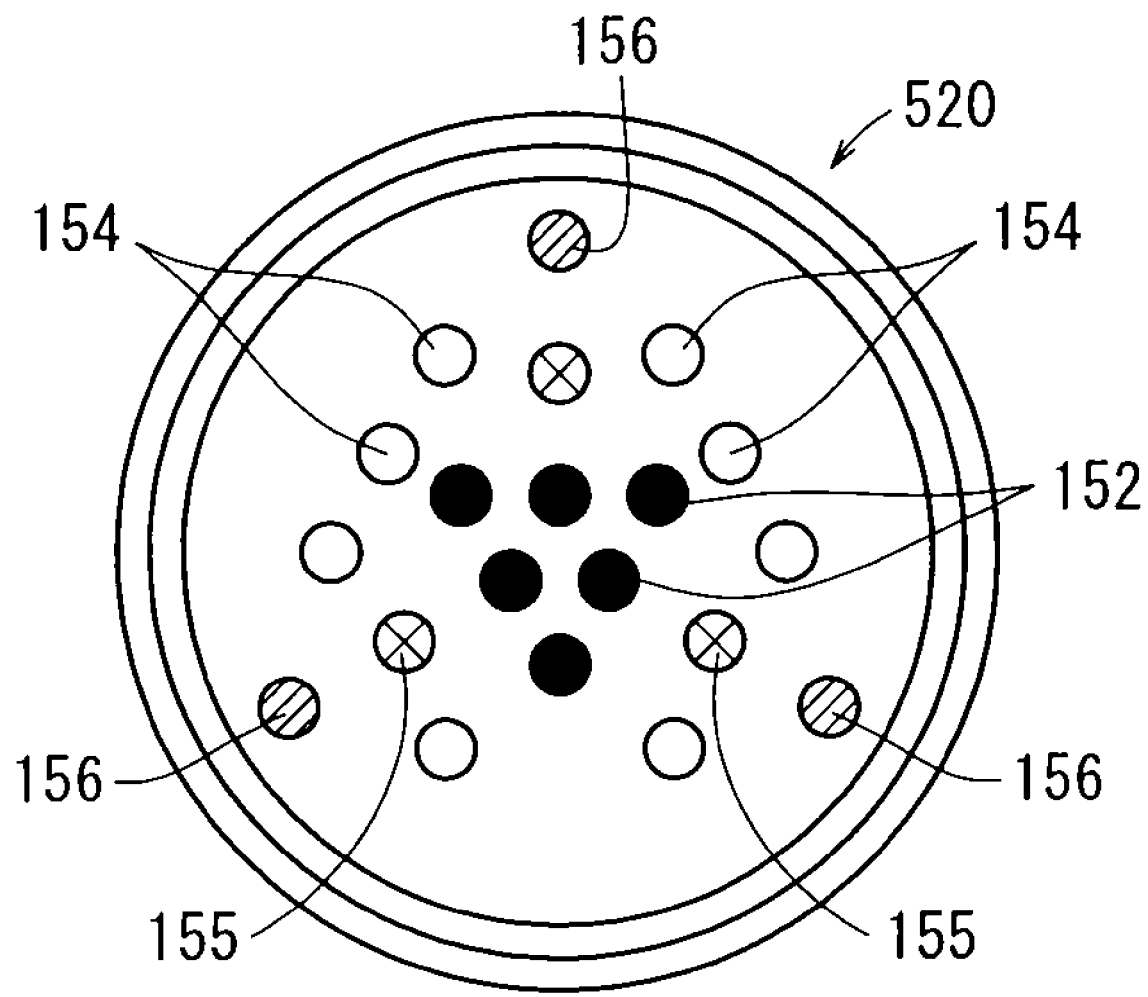
FIG. 9 is a frontal plan view of a connector.

As shown in FIG. 9, the connector 520 includes twenty pins. Among these pins, six electrical power pins 152 indicated by the filled-in circles in FIG. 9 comprise power lines corresponding to positive and negative terminals, respectively, for driving the motors 40, 41 and 42, and are arranged in a concentrated fashion in a center portion of the connector 520. The electrical power pins 152 serve to connect the motors 40, 41 and 42 with the driver 116.

Eight first signal pins 154 indicated by the blank (non-filled) circles in FIG. 9 comprise signal lines corresponding to A-phase and B-phase signals from each of the angle sensors 43, 44 and 45, along with a common circuit power source Vcc and Gnd signals, which are arranged in a surrounding manner around the electrical power pins 152. The first signal pins 154 connect the angle sensors 43, 44 and 45 with the computing section 110.

Three second signal pins 155 indicated by the X-marked circles in FIG. 9 comprise lines that indicate the operation signals from the trigger lever 32 and the compound input section 34, the diametrical positioning of which is set substantially the same as that of the first signal pins 154. The circuit power source Vcc and Gnd of the second signal pins 155 are common with those of the first signal pins 154.

Three ID pins 156 indicated by hatching in FIG. 9 comprise ID lines corresponding to the 3 bits of the ID retaining section 104, which are arranged at substantially equal intervals along the circumferential edge of the connector 520. That is, compared to the electrical power pins 152, the first signal pins 154, and the second signal pins 155, the ID pins 156 are arranged on the outermost side diametrically.

Figure 10:
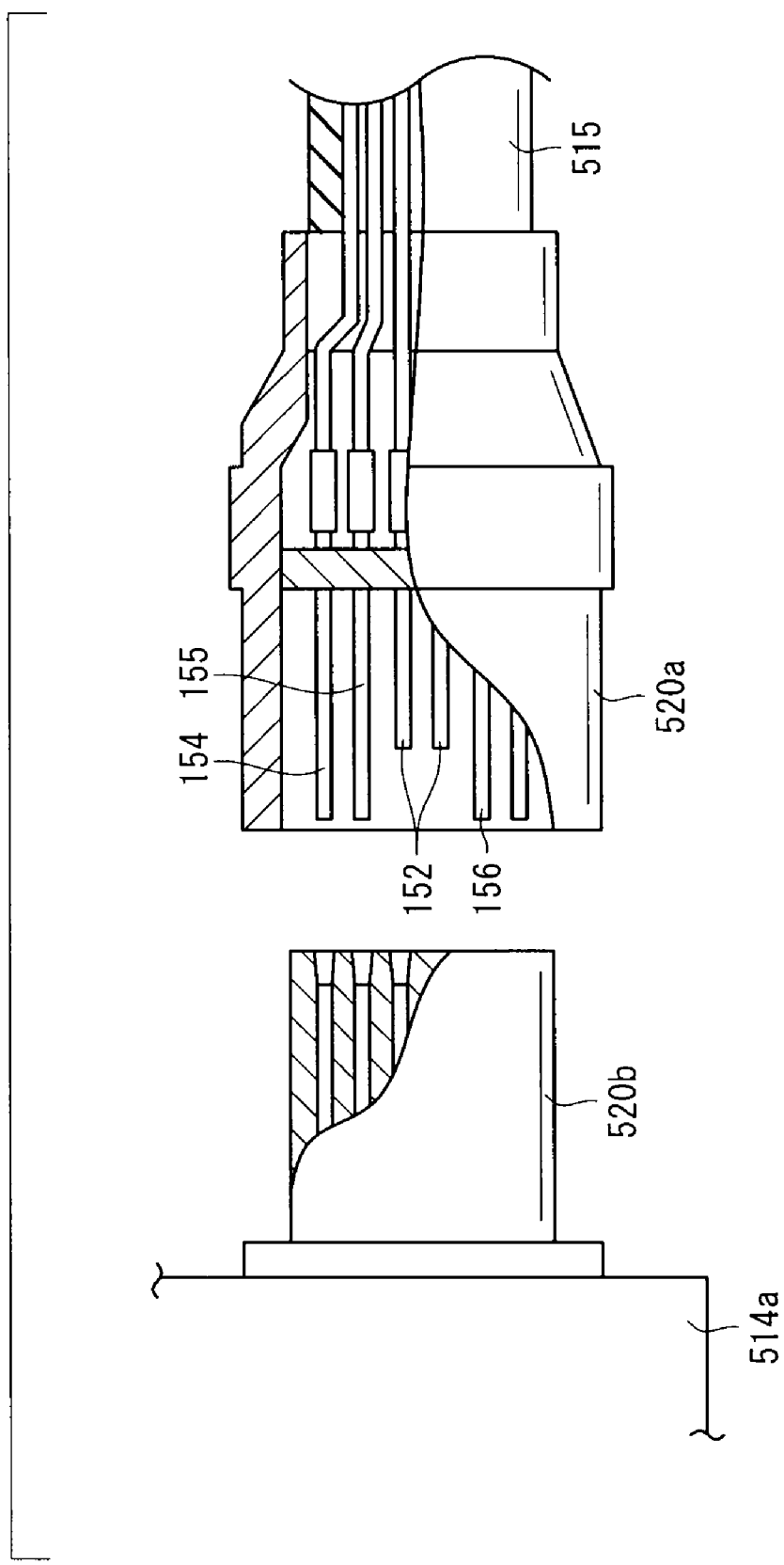
FIG. 10 is a side view of the connector.

As shown in FIG. 10, the connector 520 is constituted by a plug 520a and a receptacle 520b. In this case, the pins are each defined by male portions on the side of the plug 520a and female portions on the side of the receptacle 520b. Further, the electrical power pins 152 in the receptacle 520b are formed to be shorter than the first signal pins 154, the second signal pins 155 and the ID pins 156. More specifically, when the plug 520a and the receptacle 520b are separated from each other, first, the male and female parts of the electrical power pins 152 are separated, thereby rendering the motors 40, 41 and 42 in a non-excited state, and thereafter, the male and female parts of the first signal pins 154, the second signal pins 155 and the ID pins 156 are separated from each other. Accordingly, signals from the angle sensors 43, 44 and 45 are not cutoff in midstream while the motors 40, 41 and 42 remain in an excited state, and therefore the drive system is prevented from being placed in an open-loop condition.

Accordingly, even if the power source supply of the control apparatus 514a remains ON, when the connector 520 is attached and detached, the end effector 12 does not move unnecessarily, which is convenient when frequent detachments/reattachments are carried out. In particular, the power supply of the control apparatus 514a can be maintained in an ON state, without the trouble of operating the power switch, while in addition rebooting of the computing section 110 is not required, so that surgical procedures can be resumed and carried out quickly.

As described in further detail below, when the male and female parts of the ID pins 156 are separated, it is recognized by the computing section 110 of the control apparatus 514a that the working units 15a to 15d or the manipulator 10 has been detached, whereupon the power supply to the driver 116 is halted. Therefore, the ID pins 156 may also be set to have a shorter length. That is, when the male and female parts of the ID pins 156 are separated, the power supply to the driver 116 is stopped and the motors 40, 41 and 42 are rendered non-excited. Accordingly, similar to the case of setting the electrical power pins 152 with a shorter length, the drive system can be prevented from being placed in an open-loop condition.

Further, it is not required that the shorter pins necessarily be set on the male pin side, but rather, the female pins also may be set to have a shorter length. Stated otherwise, the lengths of each of the pins may simply be set such that, when the plug 520a and the receptacle 520b of the connector 520 are detached from one another, after the electrical power pins 152 have been disconnected, the first signal pins 154 are disconnected, or otherwise, after the ID pins 156 have been disconnected, the electrical power pins are disconnected.

Further, the three ID pins 156 are disposed on the circumferential edge of the connector, and on the outermost circumferential side compared to the other pins. Moreover, the three ID pins 156 are arranged at substantially equal angles. In accordance with such a structure, compared to the first signal pins 154 and the like, there is a high possibility that any one or two of the ID pins 156 from among the three thereof will be detached beforehand. Further, in each of the IDs, among the three bits thereof, two or more of the bits (stated otherwise, more than half the total bit number) are set to have a value of "1", such that such bits are switched instantaneously from "1" to "0". Thus, detachment of the working units 15a to 15d can be swiftly recognized by the ID identification section 120, and the power supply to the driver 116 can be very quickly stopped. Further, in cases where the bit number is greater, in order to reliably obtain this type of effect, the ID may be set such that the "1" bits are arranged insofar as possible at equal intervals, whereas both adjacent sides of the "0" bits correspond to "1" in value.

Herein, a parallel signal has been indicated as an example of a signal for the case when the ID identification signal is utilized dually also for connection recognition. However, regardless of the type of signal used, whether the signal is an analog signal or serial signal or the like, the same effect is achieved by arrangement of the signal lines thereof on the outer periphery in multiple directions.

Next, descriptions shall be given concerning operations of the manipulator system 500a constructed as described above. First, with reference to FIG. 11, an explanation shall be given in outline concerning operations when detachment operations of the working units 15a to 15d are performed. Next, detailed explanations of such operations shall be described with reference to the flowcharts of FIGS. 12 and 13.

Figure 11:
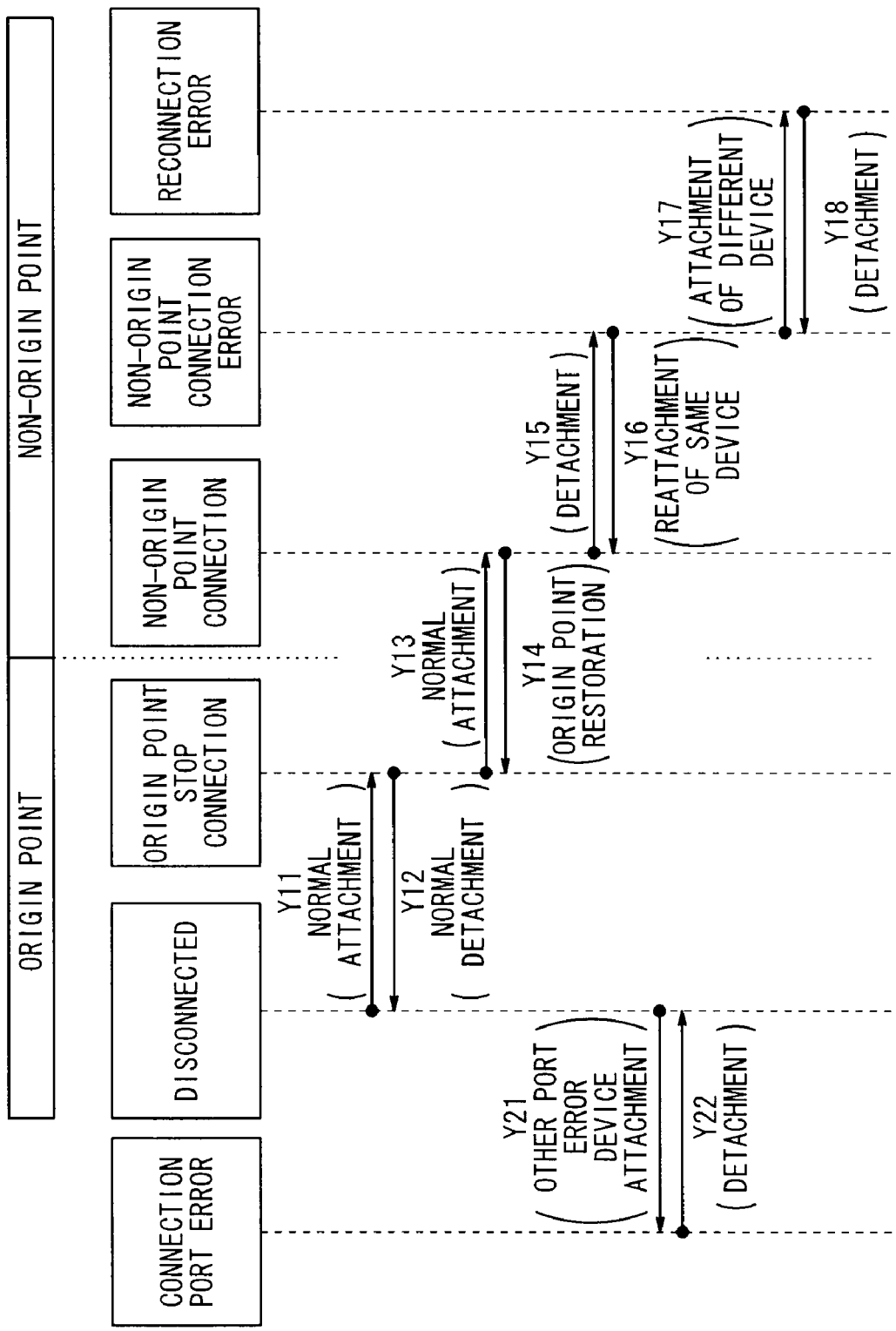
FIG. 11 is an explanatory diagram of operations in outline of the detachment operation timing of the working unit.

In FIG. 11, initially, the manipulator 10 made up of the operation command unit 14 and the working unit 15a is connected with respect to the control apparatus 514a. The surgeon performs a predetermined surgical procedure by means of the manipulator 10. In other words, the manipulator 10 is placed in a normal operational state, wherein the working unit 15a is operated in accordance with commands from the operation command unit 14 (Y13).

In the event that the working unit 15a is detached and replaced with another one of the working units 15b to 15d, once the posture of the end effector 12 of the working unit 15a is restored to its origin point posture (Y14), and after it is confirmed by the origin point recognition section 122 that the end effector 12 has been stopped at the origin point, the working unit 15a is detached from the operation command unit 14 (Y12), and is replaced by another working unit 15b to 15d (Y11). Restoration of the working unit 15a to its origin point can be displayed on the operating state display device 516, and further, can be confirmed by illumination of a lamp, which is provided on the panel surface or the like of the control apparatus 514a.

Further, assuming a case in which the working unit 15a is detached from the operation command unit 14 when the end effector 12 of the working unit 15a is in a non-origin point posture (Y15), such a condition is recognized by operations of the origin point recognition section 122 and the ID identification section 120. Such a condition is defined as a non-origin point connection error, and a detachment warning is issued by the warning section 124, thereby making the surgeon aware of the condition.

In order to return to a normal state from the non-origin point connection error condition, by reattaching the detached working unit 15a (Y16), transition is made to a normal operating condition, whereupon operations starting from the point of detachment can be continued. At this time, the non-origin point connection error and the detachment warning are canceled. In addition, assuming that the end effector 12 is first restored to its origin point posture and then stopped, a condition which is the same as the aforementioned Y14 state results, and the working unit 15a can then be detached safely and replaced with another working unit 15b to 15d.

Furthermore, while in the non-origin point error state, in the case that another working unit 15b to 15d, which differs from the detached working unit 15a, is connected (Y17), such a condition is recognized by operation of the origin point recognition section 122 and the ID identification section 120. This type of condition is defined as a reconnection error, and a misconnection warning is issued by the warning section 124, thereby making the surgeon aware of the condition.

From this condition, by detaching the misconnected working unit 15b to 15d (Y18), the reconnection error and the misconnection error warning are canceled, returning to the non-origin point error condition, and the detachment warning is generated once again.

Figure 12:
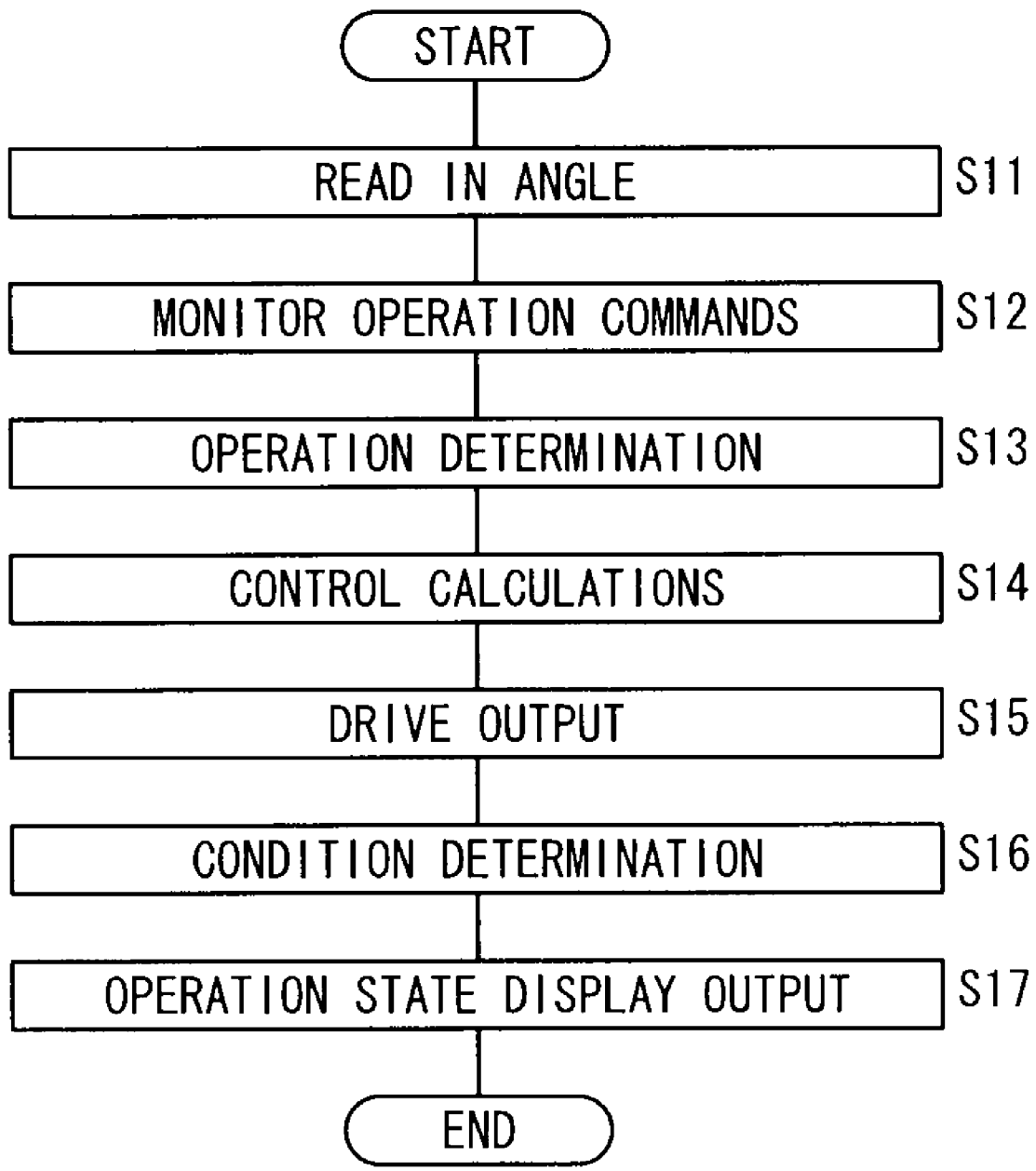
FIG. 12 is a main flowchart indicating operations of the manipulator system according to the first embodiment.

Next, the manipulator system 500a shall be explained in greater detail with reference to FIGS. 12 and 13. The manipulator system 500a is operated under an integrated control of the computing section 110 of the control apparatus 514a, which basically carries out processing in accordance with the flowchart shown in FIG. 12. The processing of FIG. 12 is executed repeatedly in accordance with a predetermined control cycle. In the following explanations, unless otherwise noted, processing is carried out in a numerical sequence of the given step numbers (or alphabetically in accordance with appended letter characters).

In step S11 of FIG. 12, outputs from the angle detectors of the operation command unit 14 and the angle detectors of the drive motors are read in by the computing section 110.

In step S12, inputs from the command input means or from the command input means 518 and the switch 118, which are provided in the control apparatus 514a, are recognized by the computing section 110.

In step S13, an operating mode of the manipulator 10 is determined based on the recognition result according to the computing section 110.

In step S14, in accordance with the determined operating mode, discrimination of motion forms and target values for the motors 40, 41 and 42 are generated. Herein, the operating modes consist of an automated mode in which predetermined operations are executed automatically, and a master/slave operating mode in which the working unit 15a is operated according to manipulations of the operation command unit 14. The motion forms consist of acceleration movements, deceleration movements, constant speed movements, stop operations and the like, in order to connect or tie together movements reliably upon switching between both of the operating modes.

In step S15, motor outputs are calculated in accordance with PID-control-based control computations from the generated control target values and the signals from the angle sensors 43, 44 and 45, which were read-in previously, and the calculated motor outputs are then supplied to the driver 116.

In step S16, various predefined conditions are compared with actual conditions read-in by the angle sensors 43, 44 and 45, and a condition determination is carried out.

In step S17, based on the determined results, outputs are carried out to the lamp provided on the control apparatus 514a, or to the operating state display device 516.

Figure 15:
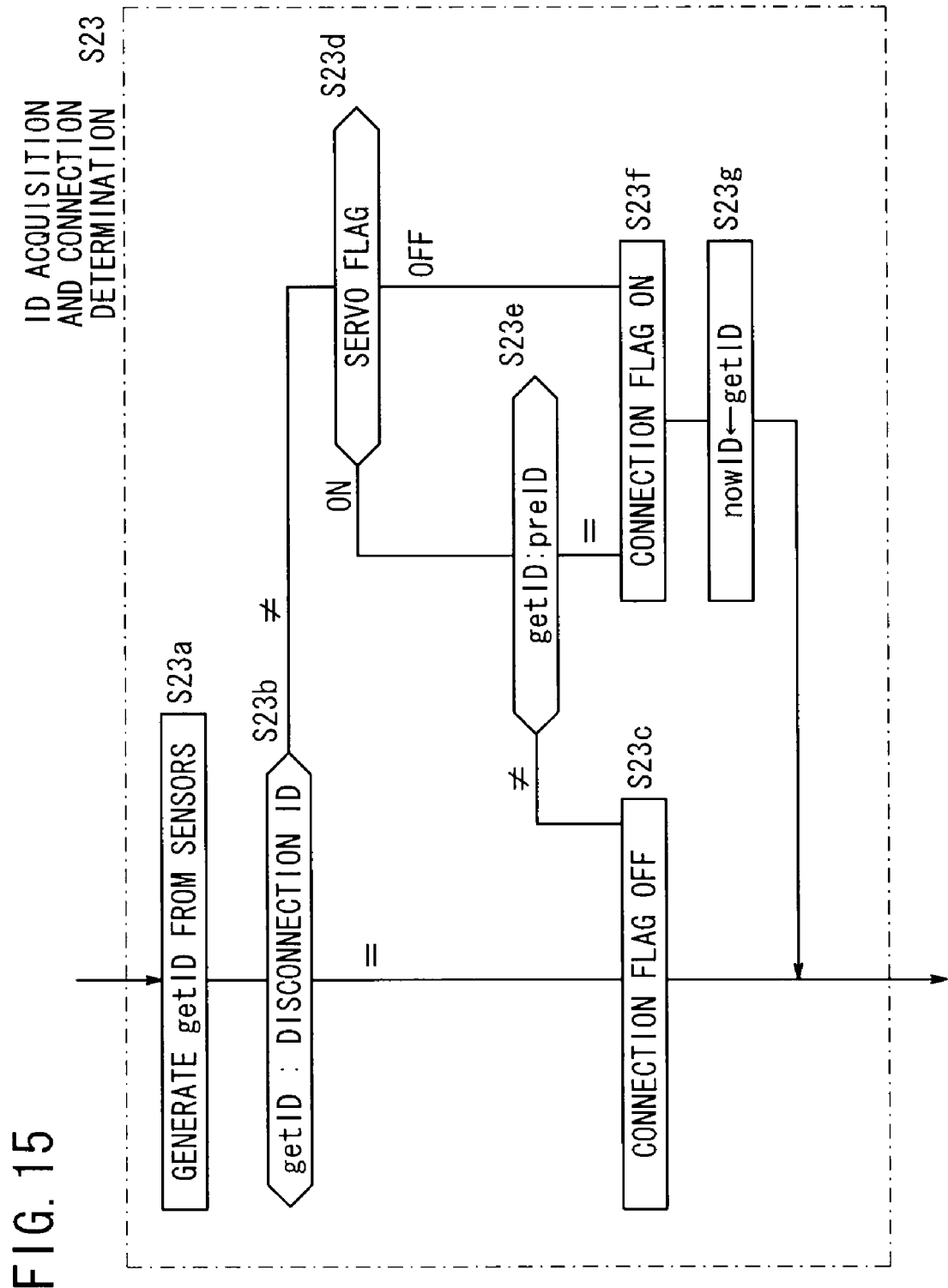
FIG. 15 is a flowchart of ID acquisition and state determining processes.

Next, determination methods for the non-origin point connection error and the reconnection error in the manipulator system 500a shall be described with reference to FIG. 13 and FIG. 15. FIG. 13 represents a further development in greater detail of a portion of the processing carried out by the conditions determination of step S16 (see FIG. 12). First, in order to discriminate the operating condition, a servo flag, a connection flag, an origin point flag, a non-origin point connection error flag, and a reconnection error flag are prepared in the control program.

During the servo condition acquisition processing of step S21, the motor excitation condition is recognized by the computing section, and the servo flag is set to ON when the motor is in an excited state, whereas the servo flag is set to OFF when the motor is in a non-excited state. If plural motors are used, servo flags may be prepared respectively for each of the motors 40, 41 and 42, and alternatively, the servo flag may be set to ON when any one of the motors 40, 41, 42 is in an excited state, whereas the servo flag is set to OFF when all the motors are in a non-excited state. Further, insofar as the number of controlled motors changes upon exchanging working units 15 having differing degrees of freedom, changes may be made suitably so as to focus on the excitation states of the motors that make up the control object.

In step S22, when the working unit 15 is in a stopped state and in its origin point posture, after an origin point restoration operation or the like, the origin point flag is set to ON, whereas the origin point flag is set to OFF when the working unit 15 is in a non-origin point posture.

In step S23, ID acquisition and connection determination processing is carried out. For facilitating understanding thereof in greater detail, step 23 is treated separately, as shown in FIG. 15.

First, in step S23a, a variable getID is generated from values that are read in and represent conditions of the ID retaining section 104 and the ID relay 106.

In step S23b, a predetermined disconnection ID is compared with the getID. The disconnection ID, for example, is a value corresponding to a state in which the sensor signals are all negative, or is a non-registered value, and in the present embodiment is standardized at $000_b$, as described previously. When the disconnection ID and the getID are equal to each other, the process sequence moves to step S23c, and when they differ from each other, the process sequence moves to step S23d.

In step S23c, the connection flag is set to OFF (connector disconnection).

In step S23d, the servo flag is confirmed. When the servo flag is ON, the process sequence moves to step S23e, and when the servo flag is OFF, the process sequence moves to step S23f.

In step S23e, the preID value, which represents a value before an ID is newly read in, is compared with the acquired getID value. When the preID value and the getID are equal to each other, the process sequence moves to step S23f, and when they differ, the process sequence moves to step S23c.

In step S23f, the connection flag is set to ON, and in step 23g, the acquired getID is recorded as a nowID, which represents the currently recognized ID value.

By means of the foregoing determination processing, the presence or absence of a connection of the working unit 15 can be confirmed from the acquired ID value. When it is judged that a connection is present, the acquired ID is stored as the nowID.

Returning to FIG. 13, in step S24, a non-origin point connection error determination process is carried out. More specifically, in step S24a, it is determined whether the connection flag is set to OFF and also whether the origin point flag is set to OFF. When such a condition arises, the process sequence moves on to step S24b, and if such a condition is not present, the process sequence moves on to step S24c.

In step S24b, a non-origin point connection error is determined and the non-origin point connection error flag is set to ON.

In step S24c, the non-origin point connection error is canceled and the non-origin point connection error flag is set to OFF. In FIG. 13, at the condition determination branch indicated by S24a, "disconnected" implies that the connection flag is OFF, while "not at origin point" implies that the origin point flag is OFF. Similarly, in the descriptions that follow, "connected" implies that the connection flag is ON, while "at origin point" implies that the origin point flag is ON.

In step S25, it is determined whether a condition exists in which the connection flag is ON and the origin point flag is ON. If this condition arises, the process sequence moves on to step S26a, and if the condition is not present, the process sequence moves on to step S26e.

The processing of steps S26a to S26d, which is carried out thereafter, is classified as step S26, in which a reconnection error determining process is performed.

In step S26a, the preID value, which represents the ID value acquired before and which was stored beforehand, and the newly acquired nowID value are both compared with each other. When the preID and nowID values are equal, the process sequence moves on to step S26d, and when different, the process sequence moves on to step S26b.

In step S26b, connection of the other working units 15b to 15d can be determined, and control parameters corresponding to such working units 15b to 15d are updated.

In step S26c, the preID value is replaced by the nowID value.

In step S26d, the reconnection error is canceled and the reconnection error flag is set to OFF.

On the other hand, in step S26e, the preID value, which represents the ID value acquired before, and which was stored beforehand, and the newly acquired nowID value are both compared with each other. When the preID and nowID values are equal, the process sequence moves on to step S26d, and when different, the process sequence moves on to step S26f.

In step S26f, because the connection of a different working unit 15b to 15d can be determined, a reconnection error is determined, and the reconnection error flag is set to ON. Thereafter, the process sequence moves on to step S27.

In step S27, it is judged whether or not any of the following conditions is fulfilled, i.e., the connection flag is OFF, the non-origin point connection error flag is ON, or the reconnection error flag is ON. If any of these conditions arises, the process sequence moves on to step S28.

In step S28, a servo OFF command is carried out whereupon motor excitation is halted. In this case, as described previously, the motors may be released by circuitry, or depending on the circumstances, the motors may also be stopped by means of an electromagnetic break caused by short-circuiting.

Figure 13:
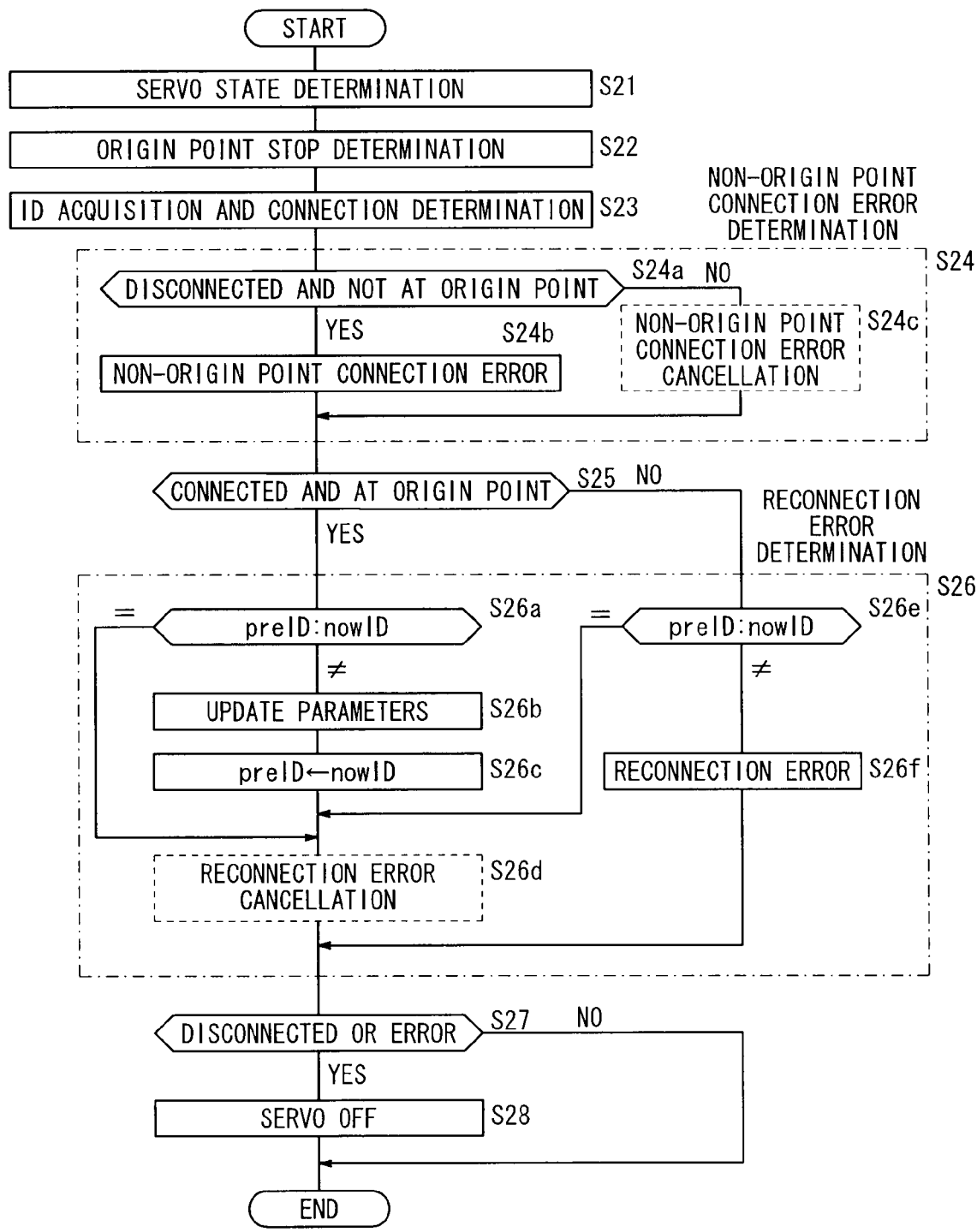
FIG. 13 is a flowchart of a state determining process in the manipulator system according to the first embodiment.

In the event that the conditions of step S27 do not arise, and after step S28, the current processing shown in FIG. 13 is brought to an end. In FIG. 13, at the condition determination branch indicated by S27, "error" implies either that the non-origin point connection error flag is ON or that the reconnection error flag is ON.

The servo OFF processing may be effected by further separating out certain conditions. For example, when the working unit 15a and the operation command unit 14 are attached and detached, since cutting off of the closed loop condition in the motor control is not included therein, it is not strictly necessary for excitation of the motors to be forcibly stopped. On the other hand, when the working unit 15a and the control apparatus 514a are attached and detached via the connector 520, since cutting off of the closed loop condition in the motor control is included therein, processing to stop the power supply is essential. Furthermore, so that the working unit 15 is exchanged in a normal manner, in particular so that the exchange and replacement of the working unit 15 is brought about reliably, and so that excitation of the motors 40, 41 and 42 is halted under an origin point stop condition, a condition in which the origin point flag is ON may also be included in the conditions for execution of the servo OFF processing. Further, in the servo OFF processing, by storing the control target values for the motors 40, 41 and 42, together with the read-in values of the angle sensors 43, 44 and 45, operations can be continued after cancellation of the non-origin point connection error.

Figure 14:
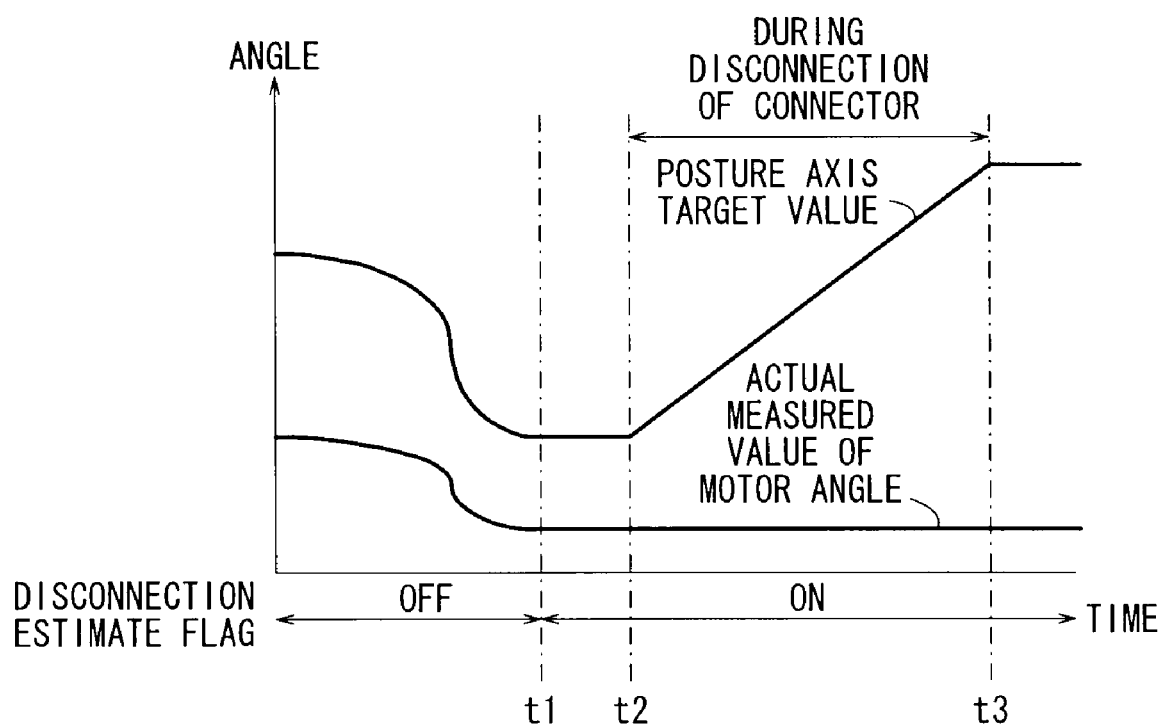
FIG. 14 is a time chart of posture axis target values at a time when the connector is detached, together with actually measured motor angle values.

Processing at the time of detachment of the operation command unit 14 is described in further detail with reference to FIG. 14. In FIG. 14, time t1 represents the oldest time having the control variables that are the same as those at the time of disconnection, time t2 is the actual disconnection time, and time t3 is the time when disconnection is confirmed by the operation command unit sensors.

In the manipulator system 500a, detachment of the operation command unit 14 is judged by analog values that are output from the devices (i.e., the trigger lever 32, the input sensors 39a, 39b, 39c of the compound input section 34) of the operation command unit 14. When the connector 520 is pulled out, as shown in FIG. 14, because an analog value of the actually measured value of the input sensor changes continuously, the posture axis target value, which is a function thereof, also varies continuously. The actually measured value of the motor angle is measured by an encoder, for example.

On the other hand, by disconnecting the connector 520, the motor line is actually severed and the motor is stopped, whereupon the encoder counter also is stopped. That is, the time at which the motor actually is disconnected and the disconnection time as judged by the analog output are different, and therefore, the posture axis target value of the judged time differs from the actual motor condition. Accordingly, when the value at this time is stored and utilized at the time of reconnection, generation of an error between the target value and the actual angle is likely to occur.

As a response to this phenomenon, when reconnecting, a method may be considered in which the actually measured encoder value is used as a new target value. However, because a control deviation, though small, is generated between the target value and the actual measured value, as a result of this error accumulating upon repeated attachments and detachments, shifting of the posture axis target value from the actually desired angle (absolute angle) tends to occur. Thus, in order to eliminate such a shift in the posture axis target value, the time of actual disconnection is estimated, and then the posture target value at that time is utilized at the time of reconnection.

Although precisely specifying the actual disconnection time t2 is difficult, it is possible to estimate the motor angle at the time t2 highly accurately. More specifically, at the control cycle or at a fixed interval greater than the control cycle, if there is no difference between the actual measured value of the motor angle of the driver and the sampled value of the previous cycle, the motor is stopped, and if such a situation is generated simultaneously for all three motors, a disconnection estimate flag is set to ON. If a difference is generated for any one of the motors, the disconnection estimate flag is set to OFF. A time that is tracked back temporally in a period during which the motor is stopped at the same angel as the angle when disconnection is judged, varies with the amount of correction. However, the target value of the time that is maximally tracked back temporally in the period during which the disconnection estimate flag is ON, may be considered to be the same as when actually disconnected. Accordingly, upon reconnection, by utilizing the target value that is obtained at this point in time, also after the connection is made, the target value remains connected or joined continuously without problems, and operations can be continued.

Now, explanations shall be made while organizing and establishing correspondence between the processes shown in FIG. 11 and FIG. 13. The process flow during normal operation (Y13) in FIG. 11 is represented as follows in FIG. 13: S21→S22→S23 (S23a→S23b→S23d→S23e→S23f→S23g)→S24a→S24c→S25→S26a→S26d→S27.

The process flow during normal detachment (Y12) of the device in FIG. 11 is represented as follows in FIG. 13: S21→S22→S23 (S23a→S23b→S23c)→S24a→S24c→S25→S26e→S26d→S27.

The process flow during normal attachment (Y11) of the device in FIG. 11 is represented as follows in FIG. 13: S21→S22→S23 (S23a→S23b→S23d→S23f→S23g)→S24a→S24c→S25→S26a→S26b→S26c→S26d→S27.

The process flow upon a non-origin point connection error (Y15) in FIG. 11 is represented as follows in FIG. 13: S21→S22→S23 (S23a→S23b→S23d→S23e→S23c)→S24a→S24b→S25→S26e→S26d→S27→S28.

The process flow upon cancellation of the non-origin point connection error (Y16) in FIG. 11 is represented as follows in FIG. 13: S21→S22→S23 (S23a→S23b→S23d→S23f→S23g)→S24a→S24c→S25→S26e→S26d→S27.

The process flow upon a reconnection error (Y17) in FIG. 11 is represented as follows in FIG. 13: S21→S22→S23 (S23a→S23b→S23d→S23f→S23g)→S24a→S24c→S25→S26e→S26f→S27→S28.

The process flow upon cancellation of the reconnection error (Y18) in FIG. 11 is represented as follows in FIG. 13: S21→S22→S23 (S23a→S23b→S23c)→S24a→S24b→S25→S26e→S26d→S27→S28.

Next, descriptions of a manipulator system 500b and a control apparatus 513b therefor according to a second embodiment shall be presented with reference to FIGS. 16 to 20. Elements of the manipulator system 500b which are the same as those of the manipulator system 500a shall be designated using the same reference characters, and detailed descriptions of such features shall be omitted.

Figure 16:
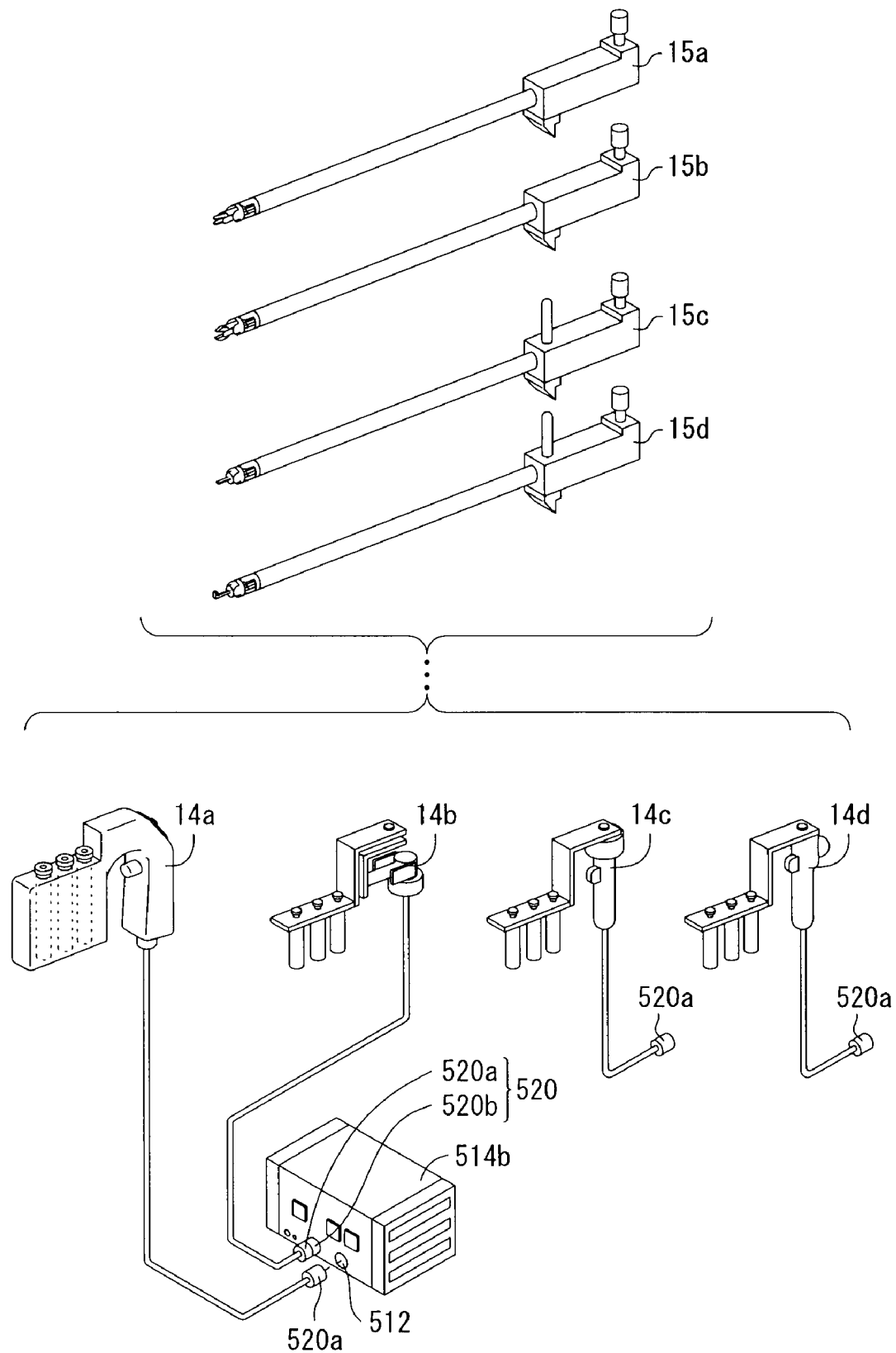
FIG. 16 is an explanatory diagram pertaining to assembly of a structure of the manipulator system according to a second embodiment of the present invention.

As shown in FIG. 16, in the manipulator system 500b, in place of the control apparatus 514a of the manipulator system 500a (see FIG. 2), a different control apparatus 514b is used. That is, the manipulator 10 (see FIG. 3), the operation command units 14a to 14d, and the working units 15a to 15d can be used as well in the manipulator system 500a.

The control apparatus 514b includes another receptacle 512, in addition to the receptacle 520b. The receptacle 520b and the receptacle 512 both have the same structure, and the plug 520a of the operation command units 14a to 14d is capable of connection with either one of the receptacle 520b or the receptacle 512. The receptacle 520b and the receptacle 512 are both available for use simultaneously, so that a surgeon can utilize two manipulators 10 corresponding to separate surgical techniques, and moreover, can operate the manipulators simultaneously. As a matter of convenience, the side connected to the receptacle 520b shall be referred to as the first manipulator (control object) 10a, while the side connected to the receptacle 512 shall be referred to as the second manipulator (control object) 10b. Further, the receptacle 520b and the receptacle 512 may also be referred to as connection ports.

Basically, the first manipulator 10a and the second manipulator 10b can be controlled independently by the control apparatus 514b. Operations can be preformed as freely as if a surgeon were provided with two of the aforementioned manipulator systems 500a. As shall be described later, in the control apparatus 514b, a cooperative check is carried out upon attachment/detachment of each of the working units 15 of the first manipulator 10a and the second manipulator 10b, so that a manipulator is not detached in a state where it is not restored to its origin point position and then mounted in another connection port. Further, corresponding to the given mode of operation, the control apparatus 514b may control the first manipulator 10a and the second manipulator 10b to be operated together cooperatively or in a coordinated fashion.

Figure 17:
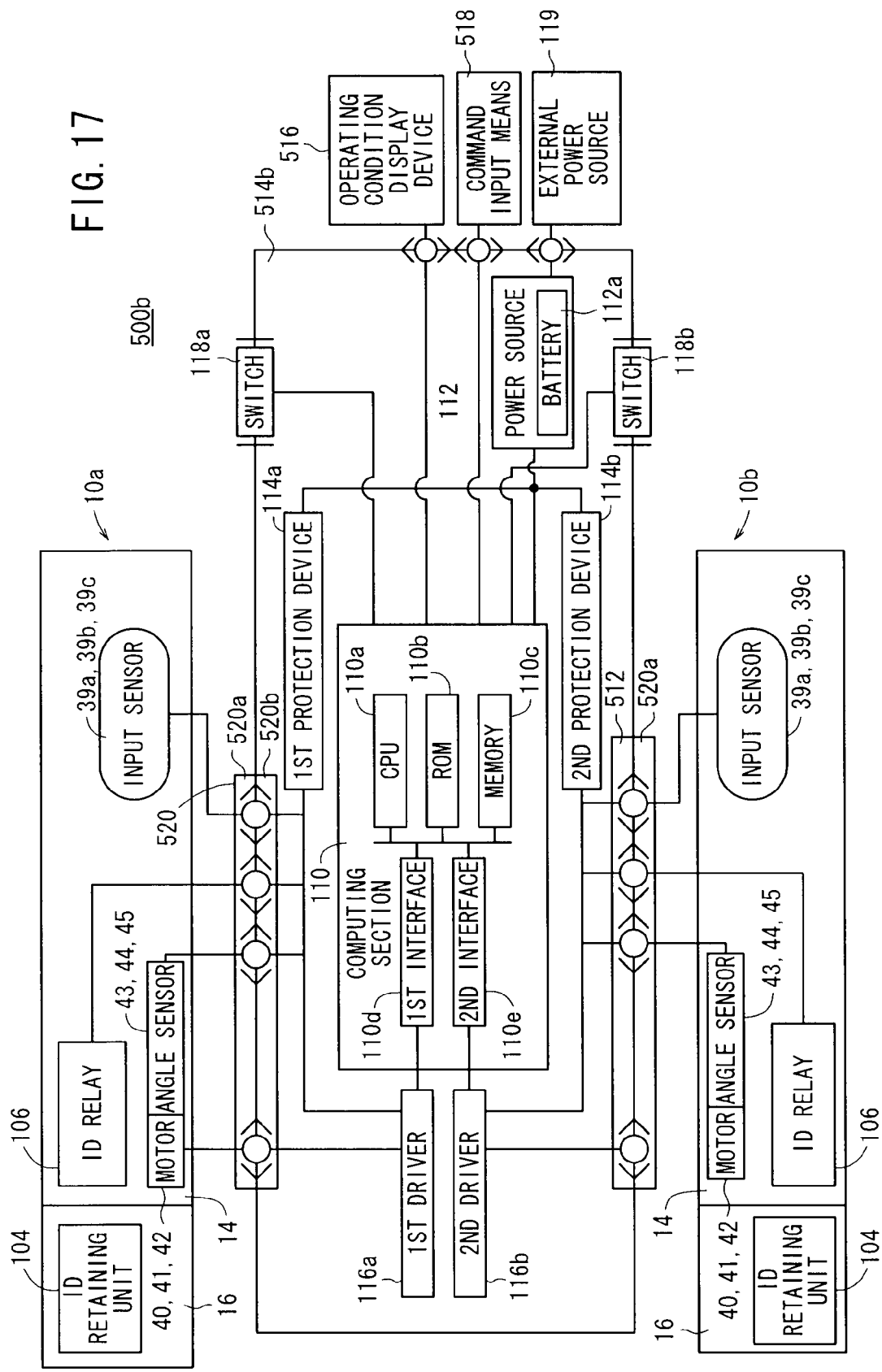
FIG. 17 is a structural block diagram of a control apparatus for the manipulator system according to the second embodiment.

As shown in FIG. 17, the control apparatus 514b includes a computing section 110, a power supply 112, a first protection device 114a, a second protection device 114b, a first driver 116a, a second driver 116b, a first switch 118a, and a second switch 118b.

The first protection device 114a and the second protection device 114b are of substantially the same structure as the protection device 114, whereas the first driver 116a and the second driver 116b have substantially the same structure as the driver 116. The first protection device 114a serves to protect the first driver 116a and the first manipulator 10a. The second protection device 114b serves to protect the second driver 116b and the second manipulator 10b. The first driver 116a carries out driving of the first manipulator 10a, while the second driver 116b carries out driving of the second manipulator 10b.

The internal structure of the computing section 110 shall be explained. The computing section 110 includes a CPU 110a, a ROM 110b, a RAM 110c, a first interface 110d, and a second interface 110e, each of which is connected respectively to a bus. The RAM 110c is broadly defined as a read/write means. For example, a non-volatile memory may be used for the RAM 110c.

The first interface 110d and the second interface 110e supply commands obtained from the CPU 110a to the first driver 116a and the second driver 116b, and also supply predetermined information back to the CPU 110a.

The CPU 110a of the computing section 110 reads and executes programs, which are recorded in the ROM 110b, etc., and controls operations of the first manipulator 10a and the second manipulator 10b by means of software processing.

In FIG. 17, although the operating state display device 516 and the command input means 518 are shown as a set corresponding to the two manipulators 10a and 10b, it is also acceptable if a set thereof is provided for each of the manipulators 10a, 10b, in which case, confirmations via the displays are made easier.

Figure 18:
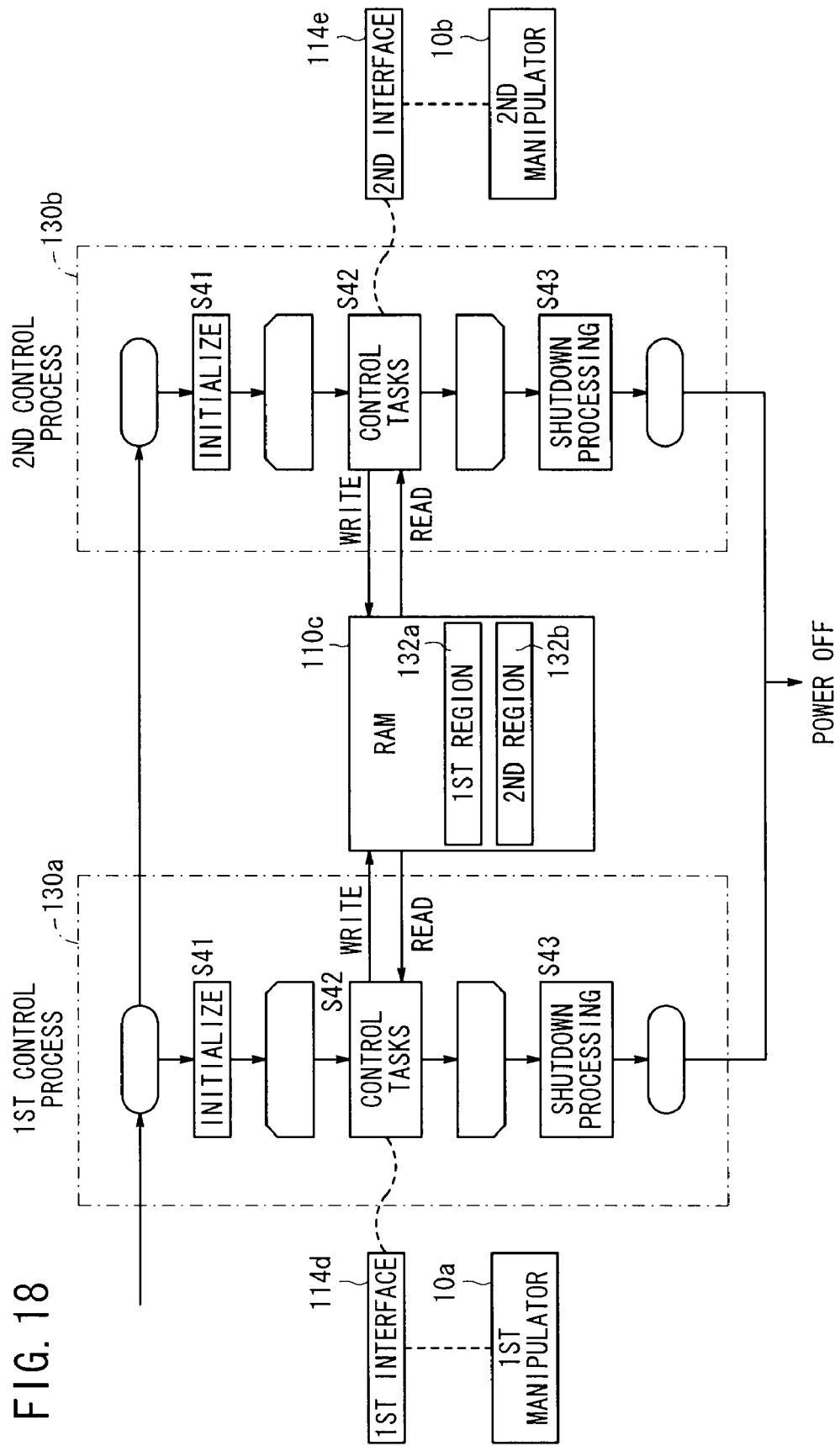
FIG. 18 is an explanatory diagram of a relationship between a first control process and a second control process.

As shown in FIG. 18, the software processing is such that control of the first manipulator 10a is carried out by a first control process 130a, and control of the second manipulator 10b is carried out by a second control process 130b.

The first control process 130a and the second control process 130b basically carry out the same program tasks, and differ only partially in their corresponding input/output ports and access addresses with respect to the RAM 110c. The RAM 110c serves as a common or shared memory, which is capable of being commonly accessed by the first control process 130a and the second control process 130b.

The first control process 130a and the second control process 130b may also comprise two substantially different programs, wherein a common processor may be of a form that uses the same library (e.g., DLL format). A single program may be expanded over two address locations and operated separately, or other means thereof may be utilized. In any of these cases, the first control process 130a and the second control process 130b are operable simultaneously and in parallel via a multitasking means or the like, wherein both the first manipulator 10a and the second manipulator 10b are structured so as to be controllable in real time. The first control process 130a and the second control process 130b are controlled basically as shown in FIG. 19.

Figure 19:
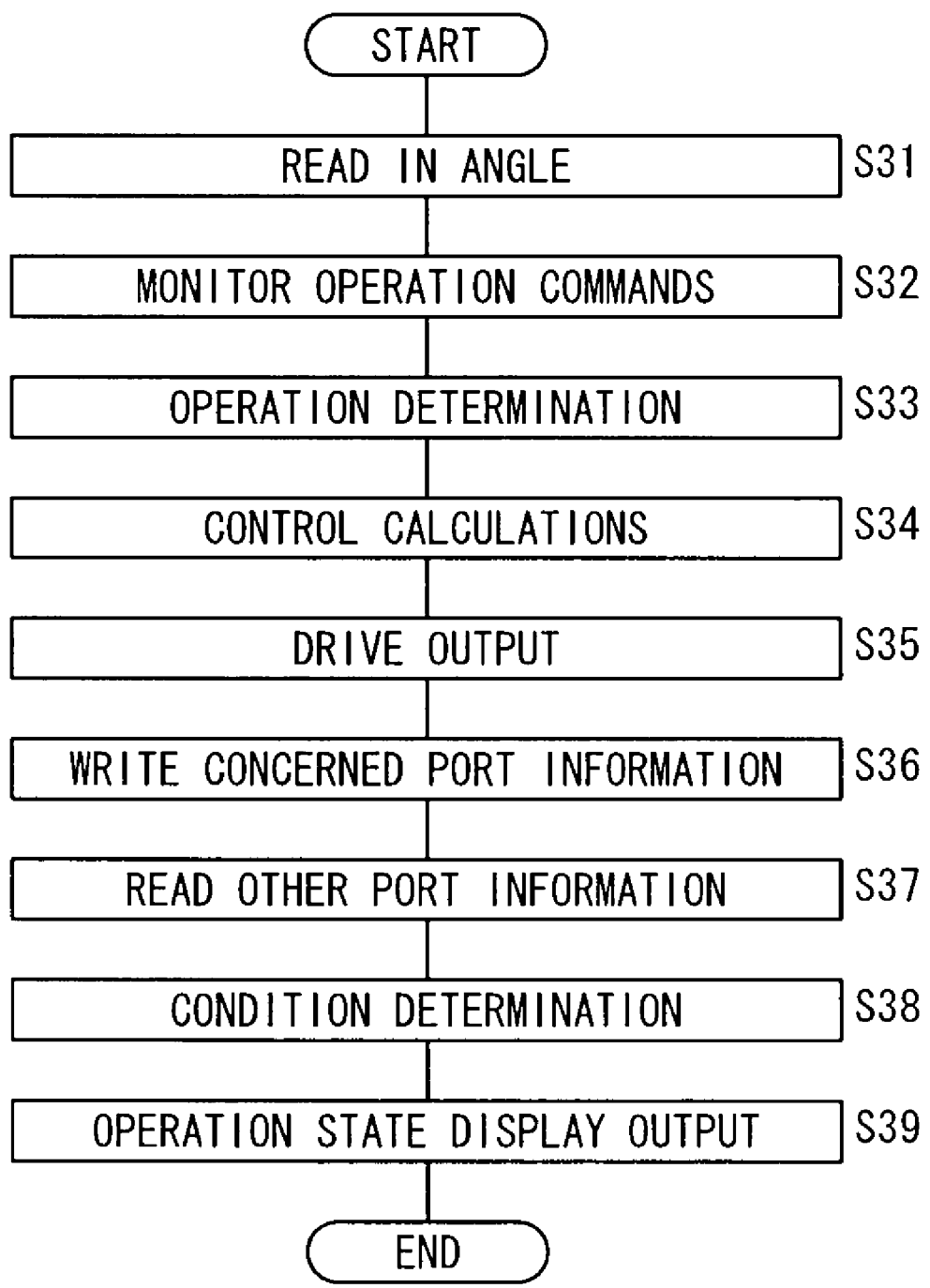
FIG. 19 is a main flowchart indicating operations of the manipulator system according to the second embodiment.
Figure 20:
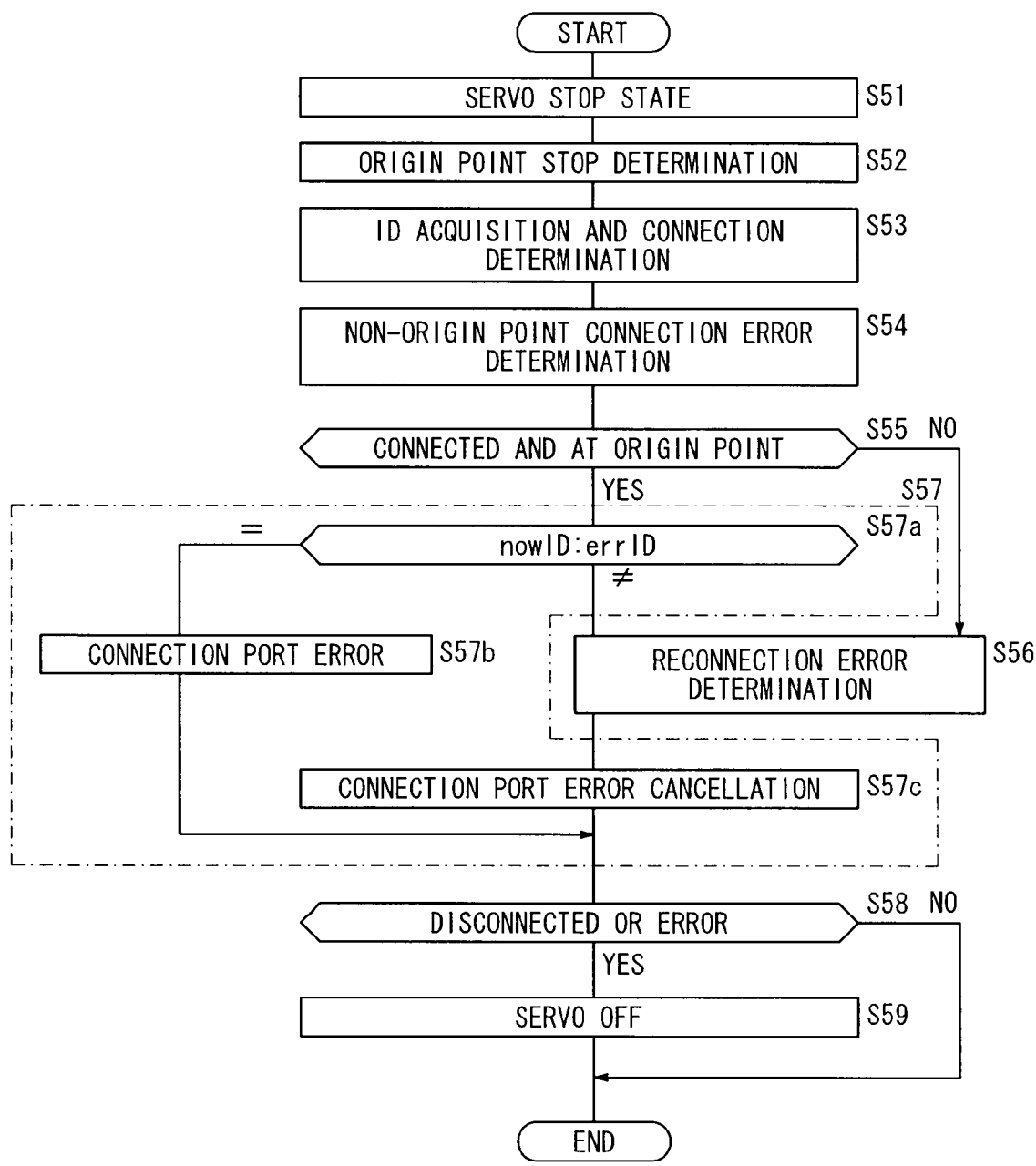
FIG. 20 is a flowchart of a state determining process in the manipulator system according to the second embodiment.

Steps S31 to S35 of FIG. 19 perform processing in the same manner as the aforementioned steps S11 to S15.

Thereafter, in step S36, the first control process 130a and the second control process 130b write data, pertaining to information of various types of flag conditions, control target values, motor angles, operation command angles, etc., which represent states at the concerned connection port managed by the processes, to predetermined write regions of connection port portions of the RAM 110c.

In step S37, another region within the RAM 110c, in which data are written by other control processes managing the other connection port, is accessed, and conditions of the other control processes are read.

Thereafter, steps S38 and S39 perform processing in the same manner as the aforementioned steps S16 and S17.

Next, returning again to FIG. 18, explanations shall be presented concerning the processing performed by the first control process 130a and the second control process 130b, which are executed at each of the connection ports. First, when electrical power is input to the control apparatus 514b, the first control process 130a and the second control process 130b are initiated. The number of initiated control processes, however, is not limited to two, and any number of processes may be initiated in accordance with the number of manipulators and connection ports that are used.

In step S41, correspondences between interfaces accessed by the first control process 130a and the second control process 130b and the connection ports are defined and set up beforehand, so that when the processes are initiated, they may be imparted as variables (or arguments). Each of the initiated processes undertakes initialization processing, in order to initialize variables, as well as to read-in control parameters, etc.

In step S42, each of the control tasks is executed. The control tasks basically carry out the processing shown in FIG. 19, by way of loop processing in which the process is performed repeatedly at a fixed cycle.

Reading and writing of interfaces, which are allocated to the first control process 130a and the second control process 130b, is carried out, and the first manipulator 10a and the second manipulator 10b connected to the interfaces are controlled.

Further, respective control processes access the RAM 110c and perform writing of predetermined information. As examples of information from the connection ports, which are written to the RAM 110c, connection flags, non-original point connection error flags, reconnection error flags, connection port error flags (discussed below), control error codes, operation command unit IDs, working unit IDs, control target values for the motors 40, 41 and 42, operating angles, and operating axis angles generated by the operation command unit 14, etc., may be given.

The control error codes represent errors codified relating to motor controls such as excessive motor speed, excessive positional deviation, excessive torque output, etc., based on information obtained by various condition determinations (step S38).

One of the control processes accesses the RAM 110c, while the control process performs reading of the above information, which has been written to the RAM 110c by the other control process. More specifically, with respect to the first control process 130a, a predetermined first region (warning region) 132a of the RAM 110c is allocated for writing, whereas a predetermined second region (warning region) 132b is allocated for reading. By contrast, with respect to the second control process 130b, the first region 132a is allocated for reading, whereas the second region 132b is allocated for writing. By utilizing the RAM 110c in this manner, respective information from each of the control processes can be exchanged.

In step S43, when a system stop (shutdown) command is input by a command from the operator, the first control process 130a and the second control process 130b carry out shutdown processing so as to cut off communications between the control processes, as well as to cut off access to the interfaces, and the like. As judgment conditions when all of the control processes are shutdown, via the RAM 110c, in all of the connection ports it is determined whether or not errors have been generated, whether the working units have been stopped at their origin points, and whether motor excitation has been halted. It is confirmed that any connected working units 15 have been shutdown while stopped at their origin points in accordance with normal procedures. When any of these conditions is not established, without shutting down the system, the number of the corresponding connection port is displayed on the operating state display device 516.

In this manner, by means of execution management at each of the connection ports, such management being divided over the first control process 130a and the second control process 130b, a fail-soft system can be constructed.

Further, because the interfaces, drivers, and protection devices are disposed at each of the connection ports, the availability of the system is high. On the other hand, the computing section 110 including the CPU 110a provides a structural element of high reliability, and by utilizing the computing section 110 in common, the cost and availability of the system can be balanced. Further, by configuring the apparatus so that the control processes are allocated to each of the connection ports, the system can respond flexibly to expansions in the number of connection ports, and the development efficiency and function expandability of the system are excellent.

Each of the connection ports possesses an interface, driver and protection device, wherein the respective control processes thereof can individually halt the supply of electrical power to the driver 116a and the second driver 116b, and can perform switching of motor excitations. As conditions for stopping the supply of electrical power to each of the drivers, the aforementioned first through third conditions may be applied.

As a result, in the event that the end effectors 12 of both the first manipulator 10a and the second manipulator 10b are in their respective origin point postures, in the event that both working units 15 are detached, or in the event that both are detached from the control apparatus 514b, the supply of electrical power to the first driver 116a and the second driver 116b is stopped, whereby the consumption of electrical power can be suppressed.

Further, in the event that the end effector 12 of either one of the first manipulator 10a and the second manipulator 10b is in its origin point posture, in the event that either one of the working units 15 is detached, or in the event that either one is detached from the control apparatus 514b, supply of electrical power of only the corresponding one among the first driver 116a and the second driver 116b, is stopped, whereby the consumption of electrical power thereby can appropriately be suppressed.

In the foregoing example, a manipulator system 500b having two connection ports was described, and however, three or more connection ports may also be provided. In laparoscopic surgeries, there are cases in which three or more manipulators are used, or even in cases where only two manipulators are used at a time, it may be appropriate to provide a greater number as spare units, or in preparation for a next surgical technique.

Further, as a result of controlling two, or even three or more, manipulators by a single control apparatus 514b, the computing section 110 and the like are used in common, and therefore the effect of suppressing electrical power consumption is great.

Incidentally, in the case of a multiple connection system in which plural manipulators can be operated simultaneously as in the manipulator system 500b, both the connection ports at which errors are not generated and the connection ports at which errors are generated are in a mixed condition, and even when under this condition, information must be supplied appropriately to the surgeon.

As such a condition, more specifically, in the case that a non-origin point connection error is generated in one of the connection ports, in order to cancel the error, the working unit 15 which caused generation of the error must be connected appropriately to the same port where it was before, and measures must be taken in such that the working unit 15 is not connected to an unconnected port without the error generated and that operations are not restarted therein. In the working unit 15 that caused the non-origin point connecting error to occur, although the phase thereof is shifted (i.e., the working unit 15 is in a non-origin point position), when the working unit 15 is connected to a normal port, the current posture thereof is set to (i.e., established as) the origin point, and movements may be commanded that deviate from the true movement range of the working unit 15, which would be undesirable.

Normally, the working unit 15 whose phase is shifted cannot be connected to an operation command unit 14 which has been stopped properly, and however, there is a concern that an external force may be applied to the working unit 15 so that the phase of the working unit is restored, and that the phase is made to match in accordance with forcibly joining the working unit 15 to the operation command unit 14 when the phase thereof is still slightly shifted. In order to avoid this type of situation, a case wherein a working unit 15, for which a non-origin point connection error occurred at another connection port, is connected to a connection port having a normal state (indicated by Y21 in FIG. 11) is defined as a connection port error, and a method to avoid such mistaken operations thereof is explained below with reference to FIG. 20. Portions of the process of FIG. 20 also correspond to the processing steps indicated previously in FIG. 13, wherein steps S51 to S56 undertake the same processing as steps S21 to S26. Further, steps S58 and S59 undertake the same processing as steps S27 and S28.

First, the other port information is read in from the RAM 110c as a common memory. If a non-origin point connection error is generated at the other port, a classifying ID indicating the occurrence of the error is read in as an errID value. The errID values are recorded only for the number of the ports at which the non-origin point connection error was generated.

The ability to connect another working unit 15 at a concerned port, at which a non-origin point error was not generated, applies to detachments when stoppage in the origin point occurs normally. Accordingly, it is first determined whether conditions are satisfied in which both the connection flag is ON and the origin point stop flag is ON (step S55). In the event these conditions are satisfied, the connection port error process is executed. As a condition in which the working unit 15 can be connected, a circumstance can be contemplated in which the concerned port also causes a non-origin point connection error, and however, in this case, when the other working unit 15, which caused the non-origin point connection error at the other port, is connected, a reconnection error is recognized.

Next, the nowID value recorded by the concerned port and the errID value are compared (S57a), and in the event both values are equal to one another, a connection port error is determined, which signifies that the working unit 15, which caused generation of a non-origin point connection error at the other port, has been connected to the concerned port, and a connection port error flag is set to ON (S57b). If the result of comparing both ID values is that the values differ from each other, then it is judged either to cancel the connection port error or that a connection port error is not to be generated. If a connection port error does exist, the connection port error is canceled and the connection port error flag is set to OFF (S57c). Insertion of the branching determination S57a is judged between the branching determination S25 and the branching determination S26 in FIG. 13.

Thereafter, similar to steps described previously, processes for condition determination and servo switching determination are carried out. The term "error" of the determination condition at the branching determination step (S58) herein implies that the non-origin point connection error flag is ON, the reconnection error flag is ON, or that the connection port error flag is ON.

The control apparatus 514b includes a function for canceling errors at each of the connection ports, for a case in which, due to some unexpected situation, a working unit 15 that lies outside of its origin posture is disconnected, and then a new working unit 15a to 15d is connected. In this case, the non-origin point connection error flag, the reconnection error flag, and the connection port error flag respectively are set to OFF, the target values and the read-in sensor angles are initialized, and the present posture is set as the origin posture.

Although a method utilizing the RAM 110c was exemplified as a configuration for enabling inter-process communications, receipt and transmission of information also can be effected by means of socket communications. Further, separate individual computing sections 110 may be provided for controlling the first manipulator 10a and the second manipulator 10b respectively, in which case, a shared memory may be provided, which is capable of being accessed in common from the two computing sections 110 (stated otherwise, the first control process 130a and the second control process 130b).

The manipulator systems 500a, 500b and control apparatus 514a, 514b have been described as pertaining to applications for medical uses in particular. However, the intended use thereof is not necessarily limited to medical applications. For example, the invention may suitably be utilized as a manipulator for repairing narrow regions of energy-related devices and the like, or may be applied to a remote operation mechanism for performing techniques through an electronic communications means or the like, from a location separated from the patient.

The control object that is controlled by the control apparatus 514a, 514b is not limited solely to the manipulators 10, 10a and 10b.

The working mechanism, manipulator and control apparatus according to the present invention are not limited to the aforementioned embodiments. It should be understood that various other configurations may be adopted without deviating from the scope of the invention as set forth in the appended claims.

What is claimed is:

1. A manipulator system equipped with a manipulator and a controller for controlling the manipulator,
    said manipulator comprising:
    an operation command unit for inputting an operation command; and
    a working unit, which is detachable with respect to said operation command unit, comprising an operating member that interacts with and is operated by an actuator of said operation command unit,
    wherein said working unit comprises an ID retaining section, which holds an ID used for individual discrimination of said working unit; and
    said controller comprising:
    an ID identification section for identifying the ID of said ID retaining section;
    a detachment determining section for determining whether or not said working unit has been detached from said operation command unit, based on the ID identified by said ID identification section;
    an origin point recognition section for recognizing whether said operating member is in a prescribed origin point position or in a non-origin point position; and
    a warning section which generates a detachment warning when it is determined, by a judgment of said detachment determining section, that said working unit has been detached from said operation command unit, in the event it is determined that said operating member is in a non-origin point position based on a signal obtained from said origin point recognition section.

2. The manipulator system according to claim 1, wherein when said detachment warning is generated, the ID obtained from said ID identification section is monitored, such that when reconnecting of said working unit is recognized and the obtained ID therefrom is equivalent to the identified ID prior to detachment, said detachment warning is extinguished, and when the obtained ID therefrom is different from the identified ID prior to detachment, a misconnection warning is generated.

3. The manipulator system according to claim 1, wherein, in the event that detachment of said working unit is determined by said detachment determining section, said controller stops supplying electrical power to the actuator that operates said operating member.

4. The manipulator system according to claim 1, wherein, in the event said origin point recognition section determines that said operating member is in the origin point position, said controller stops supplying electrical power to the actuator that operates said operating member.

5. The manipulator system according to claim 1, wherein, in the event it is determined that said operation command unit is detached, by a signal from a manually operable input means on said operation command unit, said controller stops supplying electrical power to a driver, which drives the actuator that operates said operating member.

6. The manipulator system according to claim 1, wherein, in the event said ID identification section determines that said working unit is detached, said controller supplies a stop signal to a driver, which drives the actuator that operates said operating member.

7. The manipulator system according to claim 1, wherein, in the event said origin point recognition section determines that said operating member is in the origin point position, said controller supplies a stop signal to a driver, which drives the actuator that operates said operating member.

8. The manipulator system according to claim 1, wherein, in the event it is determined that said operation command unit is detached, by a signal from a manually operable input means on said operation command unit, said controller supplies a stop signal to a driver, which drives the actuator that operates said operating member.

9. The manipulator system according to claim 1, wherein said ID retaining section is configured so as to transmit an ID while not in contact with respect to an ID detector of said operation command unit.

10. The manipulator system according to claim 1, wherein, in a manually operable input means on said operation command unit, a predetermined voltage is applied to a detector that detects an operation amount, and a predetermined range of said voltage is set as an operative range, and wherein said controller recognizes that said operation command unit has been detached based on the voltage supplied from said detector being outside of said predetermined range.

11. The manipulator system according to claim 1, wherein said detachment determining section determines that said working unit is detached when the identified ID is changed.

12. The manipulator system according to claim 1, wherein paired connectors are disposed on connection locations of said operation command unit and said controller, said paired connectors include electrical power pins for supplying electrical power to said actuator that operates said operating member, signal pins a sensor that detects a position of said operating member, and ID pins connected to said ID retaining section, wherein the length of each of said pins is set such that, when said paired connectors are detached, a male/female connection of said signal pins becomes disconnected after a male/female connection of said electrical power pins has been disconnected, or the male/female connection of said electrical power pins becomes disconnected after a male/female connection of said ID pins has been disconnected.

13. The manipulator system according to claim 1, wherein the ID is represented by a binary number made up from a plurality of bits, said ID pins being provided in a number corresponding to a bit number, said ID retaining section supplying an active signal corresponding to a specified bit of the ID to the ID detector of said operation command unit, and wherein a bit other than said specified bit is recognized as a negative signal by said ID detector.

14. The manipulator system according to claim 13, wherein said active signal is allocated to bits making up half or more of the plurality of bits of the ID.

15. The manipulator system according to claim 13, wherein said ID pins are arranged on an outermost peripheral side compared to other pins, and at substantially equal angles from each other.

16. The manipulator system according to claim 15, wherein, in said ID retaining section, the ID is set such that, among said ID pins, pins on both adjacent sides of a pin corresponding to a negative signal correspond to active signals.

17. The manipulator system according to claim 1, wherein:
said controller is configured such that at least two manipulators are capable of connection thereto;
said controller comprises a first control process section for controlling a first manipulator, a second control process section for controlling a second manipulator, and a memory means which is commonly accessible from said first control process section and said second control process section;
when said detachment warning is generated, said first control process section stores a signal in a predetermined warning region of said memory, for enabling recognition of an ID, and when said detachment warning is canceled, said signal that is stored in said warning region is deleted; and
said second control process section reads said signal from said warning region, and reads the ID stored by said first control process section, and when the ID that is obtained from the ID identification section in said second control process section is equivalent to the ID stored by said first control process section, driving of said second manipulator is prohibited.

18. The manipulator system according to claim 17, wherein said first control process section and said second control process section are operated by software, which is executed simultaneously and in parallel by the same computing section.

19. The manipulator system according to claim 18, further comprising:
a first driver for driving the actuator of said first manipulator; and
a second driver for driving the actuator of said second manipulator,
wherein said computing section is configured to enable stopping of the electrical power supply individually with respect to said first driver and said second driver.

20. A control apparatus for a control object,
said control object comprising:
an operation command unit for inputting an operation command;
a working unit, which is detachable with respect to said operation command unit, comprising an operating member that interacts with and is operated by an actuator of said operation command unit,
an ID retaining section disposed in said working unit, which holds an ID used for individualized discrimination of said working unit; and
an ID detector disposed in said operation command unit for detecting said ID,
said control apparatus comprising:
an ID identification section for identifying the ID, based on a signal supplied from said ID detector;
a detachment determining section for determining whether or not said working unit has been detached from said operation command unit, based on the ID identified by said ID identification section;
an origin point recognition section for recognizing whether said operating member is in a prescribed origin point position or in a non-origin point position; and
a warning section which generates a detachment warning when it is determined, by a judgment of said detachment determining section, that said working unit has been detached from said operation command unit, in the event it is determined that said operating member is in a non-origin point position based on a signal obtained from said origin point recognition section.

* * * * *